US009233152B2

United States Patent
He et al.

(10) Patent No.: US 9,233,152 B2
(45) Date of Patent: Jan. 12, 2016

(54) MONOCLONAL ANTIBODIES TARGETING NEUTRALIZING EPITOPES ON H5 INFLUENZA VIRUS OF CLADE 2.3

(75) Inventors: Fang He, Singapore (SG); Jimmy Hwei-Sing Kwang, Singapore (SG)

(73) Assignee: Temasek Life Sciences Laboratory Limited, Singapore (SG)

( * ) Notice: Subject to any disclaimer, the term of this patent is extended or adjusted under 35 U.S.C. 154(b) by 0 days.

(21) Appl. No.: 14/369,576

(22) PCT Filed: Jan. 12, 2012

(86) PCT No.: PCT/SG2012/000012
§ 371 (c)(1),
(2), (4) Date: Jun. 27, 2014

(87) PCT Pub. No.: WO2013/105896
PCT Pub. Date: Jul. 18, 2013

(65) Prior Publication Data
US 2014/0314777 A1    Oct. 23, 2014

(51) Int. Cl.
*C07K 16/10* (2006.01)
*G01N 33/569* (2006.01)
*A61K 39/00* (2006.01)
*A61K 39/145* (2006.01)

(52) U.S. Cl.
CPC ........... *A61K 39/145* (2013.01); *C07K 16/1018* (2013.01); *G01N 33/56983* (2013.01); *A61K 39/00* (2013.01); *A61K 2039/505* (2013.01); *C07K 2317/33* (2013.01); *C07K 2317/34* (2013.01); *C07K 2317/76* (2013.01); *G01N 2333/11* (2013.01)

(58) Field of Classification Search
CPC ................... C12N 2760/16122; A61K 39/145; A61K 39/12; A61K 2039/505; A61K 39/00; A61K 2039/525; A61K 2039/6056; C07K 14/005; C07K 16/1018; C07K 2316/96; C07K 2317/24; C07K 14/11; C07K 2317/34
See application file for complete search history.

(56) References Cited

FOREIGN PATENT DOCUMENTS

WO    2008110937 A2    9/2008
WO    2009/035420 A1    3/2009

OTHER PUBLICATIONS

Sun L, Lu X, Li C, Wang M, Liu Q, Li Z, Hu X, Li J, Liu F, Li Q, Belser JA, Hancock K, Shu Y, Katz JM, Liang M, Li D. Generation, characterization and epitope mapping of two neutralizing and protective human recombinant antibodies against influenza A H5N1 viruses. PLoS One. 2009;4(5):e5476. Epub May 7, 2009.*
Shu Y, Lan Y, Wen L, Wang D, Yao L, Li X, Wang Q, Dong J, Zhao X, Huang J, Zhang X, Nie K, Duan S, Xu W. Hemagglutinin [Influenza A virus (A/Anhui/Jan. 2005(H5N1))]. GenBank: ABD28180.1. Dep. Apr. 2, 2006.*
He F, Soejoedono RD, Murtini S, Goutama M, Kwang J. Complementary monoclonal antibody-based dot ELISA for universal detection of H5 avian influenza virus. BMC Microbiol. Dec 30, 2010;10:330.*
Sun LN, Liu QZ, Wang M, Li C, Li Z, Hu XF, Zhu LL, Li Q, Wang SW, Shu YL, Liang MF, Li DX. [Generation of neutralizing recombinant human antibodies for targeting highly pathogenic avian influenza A (H5N1) virus]. Bing Du Xue Bao. May 2008;24(3):165-71. Abstract only.*
Duvvuri VR, Duvvuri B, Cuff WR, Wu GE, Wu J. Role of positive selection pressure on the evolution of H5N1 hemagglutinin. Genomics Proteomics Bioinformatics. Jun. 2009;7(1-2):47-56.*
Yoshida R, et. al. PLoS Pathog. Mar. 2009;5(3):e1000350. Epub Mar. 20, 2009.*
Ho HT, Qian HL, He F, Meng T, Szyporta M, Prabhu N, Prabakaran M, Chan KP, Kwang J. Rapid detection of H5N1 subtype influenza viruses by antigen capture enzyme-linked immunosorbent assay using H5- and N1-specific monoclonal antibodies. Clin Vaccine Immunol. May 2009;16(5):726-32. Epub Mar. 25, 2009.*
Chen, Y. et al., "Broad Cross-Protection against H5N1 Avian Influenza Virus Infection by Means of Monoclonal Antibodies that Map to Conserved Viral Epitopes," The Journal of Infectious Diseases, Jan. 1, 2009, vol. 199, No. 1, pp. 49-58.
Sun, L. et al., "Generation, Characterization and Epitope Mapping of Two Neutralizing and Protective Human Recombinant Antibodies against Influenza A H5N1 Viruses," PLoS One, May 7, 2009, vol. 4, No. 5: e5476, pp. 1-11.
Wu, W. et al., "Antigenic Profile of Avian H5N1 Viruses in Asia from 2002 to 2007," Journal of Virology, Dec. 12, 2007, vol. 82, No. 4, pp. 1798-1807.
Prabakaran, M. et al., "Combination Therapy Using Chimeric Monoclonal Antibodies Protects Mice from Lethal H5N1 Infection and Prevents Formation of Escape Mutants," PLoS One, May 22, 2009, vol. 4, No. 5:e5672, pp. 1-10.
Oh, S. et al., "Neutralizing Monoclonal Antibodies to Different Clades of Influenza A H5N1 Viruses," Journal of Virological Methods, Jan. 17, 2009, vol. 157, No. 2, pp. 161-167.

* cited by examiner

*Primary Examiner* — Benjamin P Blumel
*Assistant Examiner* — Rachel Gill
(74) *Attorney, Agent, or Firm* — Rothwell, Figg, Ernst & Manbeck P.C.

(57) ABSTRACT

The present invention relates to murine monoclonal antibodies C, F and H which target major neutralizing epitopes of influenza H5 hemagglutinin of clade 2.3 and active fragments thereof. The present invention also relates to methods and compositions for the prophylaxis and treatment of H5N1 influenza using murine monoclonal antibodies C, F or H or active fragments thereof. The present invention additionally relates to methods and compositions for providing universal protection against H5 influenza viruses using murine monoclonal antibodies C, F or H or fragments thereof together with complementary murine monoclonal antibody or active fragments thereof. The present invention further relates to methods and compositions for the characterization and quantification of H5 expression using these murine monoclonal antibody or fragments thereof.

39 Claims, 1 Drawing Sheet

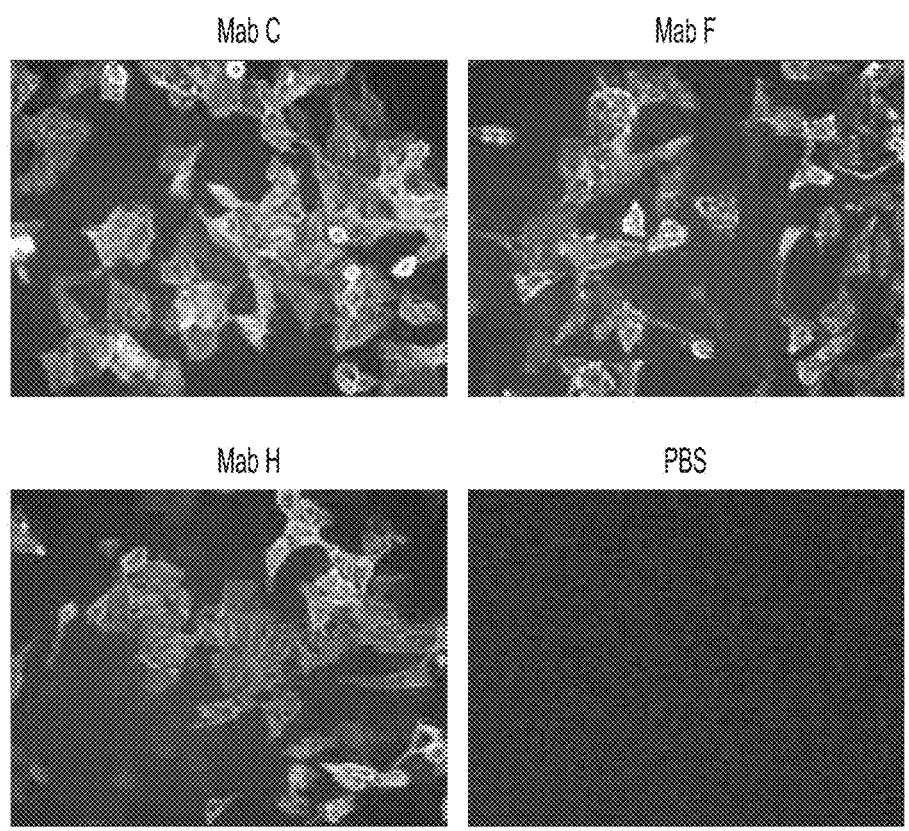

SEQUENCE LISTING

```
<160> NUMBER OF SEQ ID NOS: 4

<210> SEQ ID NO 1
<211> LENGTH: 1704
<212> TYPE: DNA
<213> ORGANISM: Influenza A virus
<220> FEATURE:
<221> NAME/KEY: CDS
<222> LOCATION: (1)..(1704)

<400> SEQUENCE: 1 atg gag aaa ata gtg ctt ctt ctt gca ata gtc agc ctt gtt aaa agt      48
Met Glu Lys Ile Val Leu Leu Leu Ala Ile Val Ser Leu Val Lys Ser
1               5                   10                  15 gat cag att tgc att ggt tac cat gca aac aac tcg aca gag cag gtt      96
Asp Gln Ile Cys Ile Gly Tyr His Ala Asn Asn Ser Thr Glu Gln Val
            20                  25                  30 gac aca ata atg gaa aag aac gtt act gtt aca cat gcc caa gac ata     144
Asp Thr Ile Met Glu Lys Asn Val Thr Val Thr His Ala Gln Asp Ile
        35                  40                  45 ctg gaa aag aca cac aac ggg aag ctc tgc gat cta gat gga gtg aag     192
Leu Glu Lys Thr His Asn Gly Lys Leu Cys Asp Leu Asp Gly Val Lys
    50                  55                  60 cct ctg att tta aga gat tgt agt gta gct gga tgg ctc ctc gga aac     240
Pro Leu Ile Leu Arg Asp Cys Ser Val Ala Gly Trp Leu Leu Gly Asn
65                  70                  75                  80 cca atg tgt gac gaa ttc atc aat gtg ccg gaa tgg tct tac ata gtg     288
Pro Met Cys Asp Glu Phe Ile Asn Val Pro Glu Trp Ser Tyr Ile Val
                85                  90                  95 gag aag gcc aac cca gcc aat gac ctc tgt tac cca ggg aat ttc aac     336
Glu Lys Ala Asn Pro Ala Asn Asp Leu Cys Tyr Pro Gly Asn Phe Asn
            100                 105                 110 gac tat gaa gaa ctg aaa cac cta ttg agc aga ata aac cat ttt gag     384
Asp Tyr Glu Glu Leu Lys His Leu Leu Ser Arg Ile Asn His Phe Glu
        115                 120                 125 aaa att cag atc atc ccc aaa agt tct tgg tcc gat cat gaa gcc tca     432
Lys Ile Gln Ile Ile Pro Lys Ser Ser Trp Ser Asp His Glu Ala Ser
    130                 135                 140 tca ggg gtg agc tca gca tgt cca tac cag gga acg ccc tcc ttt ttc     480
Ser Gly Val Ser Ser Ala Cys Pro Tyr Gln Gly Thr Pro Ser Phe Phe
145                 150                 155                 160 aga aat gtg gta tgg ctt atc aaa aag aac aat aca tac cca aca ata     528
Arg Asn Val Val Trp Leu Ile Lys Lys Asn Asn Thr Tyr Pro Thr Ile
                165                 170                 175 aag aga agc tac aat aat acc aac cag gaa gat ctt ttg ata ctg tgg     576
Lys Arg Ser Tyr Asn Asn Thr Asn Gln Glu Asp Leu Leu Ile Leu Trp
            180                 185                 190 ggg att cat cat tct aat gat gcg gca gag cag aca aag ctc tat caa     624
Gly Ile His His Ser Asn Asp Ala Ala Glu Gln Thr Lys Leu Tyr Gln
        195                 200                 205
```

-continued

```
aac cca acc acc tat att tcc gtt ggg aca tca aca cta aac cag aga    672
Asn Pro Thr Thr Tyr Ile Ser Val Gly Thr Ser Thr Leu Asn Gln Arg
    210                 215                 220 ttg gta cca aaa ata gct act aga tcc aaa gta aac ggg caa agt gga    720
Leu Val Pro Lys Ile Ala Thr Arg Ser Lys Val Asn Gly Gln Ser Gly
225                 230                 235                 240 agg atg gat ttc ttc tgg aca att tta aaa ccg aat gat gca atc aac    768
Arg Met Asp Phe Phe Trp Thr Ile Leu Lys Pro Asn Asp Ala Ile Asn
                245                 250                 255 ttc gag agt aat gga aat ttc att gct cca gaa tat gca tac aaa att    816
Phe Glu Ser Asn Gly Asn Phe Ile Ala Pro Glu Tyr Ala Tyr Lys Ile
            260                 265                 270 gtc aag aaa ggg gac tca gca att gtt aaa agt gaa gtg gaa tat ggt    864
Val Lys Lys Gly Asp Ser Ala Ile Val Lys Ser Glu Val Glu Tyr Gly
        275                 280                 285 aac tgc aac aca aag tgt caa act cca ata ggg gcg ata aac tct agt    912
Asn Cys Asn Thr Lys Cys Gln Thr Pro Ile Gly Ala Ile Asn Ser Ser
    290                 295                 300 atg cca ttc cac aac ata cac cct ctc acc atc ggg gaa tgc ccc aaa    960
Met Pro Phe His Asn Ile His Pro Leu Thr Ile Gly Glu Cys Pro Lys
305                 310                 315                 320 tat gtg aaa tca aac aaa tta gtc ctt gcg act ggg ctc aga aat agt   1008
Tyr Val Lys Ser Asn Lys Leu Val Leu Ala Thr Gly Leu Arg Asn Ser
                325                 330                 335 cct cta aga gaa aga aga aga aaa aga gga cta ttt gga gct ata gca   1056
Pro Leu Arg Glu Arg Arg Arg Lys Arg Gly Leu Phe Gly Ala Ile Ala
            340                 345                 350 ggg ttt ata gag gga gga tgg cag gga atg gta gat ggt tgg tat ggg   1104
Gly Phe Ile Glu Gly Gly Trp Gln Gly Met Val Asp Gly Trp Tyr Gly
        355                 360                 365 tac cac cat agc aat gag cag ggg agt ggg tac gct gca gac aaa gaa   1152
Tyr His His Ser Asn Glu Gln Gly Ser Gly Tyr Ala Ala Asp Lys Glu
    370                 375                 380 tcc act caa aag gca ata gat gga gtc acc aat aag gtc aac tcg atc   1200
Ser Thr Gln Lys Ala Ile Asp Gly Val Thr Asn Lys Val Asn Ser Ile
385                 390                 395                 400 att gac aaa atg aac act cag ttt gag gcc gtt gga agg gaa ttt aat   1248
Ile Asp Lys Met Asn Thr Gln Phe Glu Ala Val Gly Arg Glu Phe Asn
                405                 410                 415 aac tta gaa agg aga ata gag aat tta aac aag aaa atg gaa gac gga   1296
Asn Leu Glu Arg Arg Ile Glu Asn Leu Asn Lys Lys Met Glu Asp Gly
            420                 425                 430 ttc cta gat gtc tgg act tat aat gct gaa ctt ctg gtt ctc atg gaa   1344
Phe Leu Asp Val Trp Thr Tyr Asn Ala Glu Leu Leu Val Leu Met Glu
        435                 440                 445 aat gag aga act cta gac ttc cat gat tca aat gtc aag aac ctt tac   1392
Asn Glu Arg Thr Leu Asp Phe His Asp Ser Asn Val Lys Asn Leu Tyr
    450                 455                 460 gac aag gtc cga cta cag ctt agg gat aat gca aag gag ctg ggt aac   1440
Asp Lys Val Arg Leu Gln Leu Arg Asp Asn Ala Lys Glu Leu Gly Asn
465                 470                 475                 480 ggt tgt ttc gag ttc tat cac aaa tgt gat aat gaa tgt atg gaa agt   1488
Gly Cys Phe Glu Phe Tyr His Lys Cys Asp Asn Glu Cys Met Glu Ser
                485                 490                 495 gta aga aac gga acg tat gac tac ccg cag tat tca gaa gaa gca aga   1536
Val Arg Asn Gly Thr Tyr Asp Tyr Pro Gln Tyr Ser Glu Glu Ala Arg
            500                 505                 510 tta aaa aga gag gaa ata agt gga gta aaa ttg gaa tca ata gga act   1584
Leu Lys Arg Glu Glu Ile Ser Gly Val Lys Leu Glu Ser Ile Gly Thr
```

```
            515                 520                 525
tac caa ata ctg tca att tat tca aca gtt gcg agt tct cta gca ctg        1632
Tyr Gln Ile Leu Ser Ile Tyr Ser Thr Val Ala Ser Ser Leu Ala Leu
        530                 535                 540 gca atc atg gtg gct ggt cta tct ttg tgg atg tgc tcc aat ggg tcg        1680
Ala Ile Met Val Ala Gly Leu Ser Leu Trp Met Cys Ser Asn Gly Ser
545                 550                 555                 560 tta caa tgc aga att tgc att taa                                        1704
Leu Gln Cys Arg Ile Cys Ile
                565

<210> SEQ ID NO 2
<211> LENGTH: 567
<212> TYPE: PRT
<213> ORGANISM: Influenza A virus

<400> SEQUENCE: 2

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Thr Pro Ser Phe Phe
145                 150                 155                 160

Arg Asn Val Val Trp Leu Ile Lys Lys Asn Asn Thr Tyr Pro Thr Ile
                165                 170                 175

Lys Arg Ser Tyr Asn Asn Thr Asn Gln Glu Asp Leu Leu Ile Leu Trp
            180                 185                 190

Gly Ile His His Ser Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Asp Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Val Lys Ser Glu Val Glu Tyr Gly
        275                 280                 285

Asn Cys Asn Thr Lys Cys Gln Thr Pro Ile Gly Ala Ile Asn Ser Ser
    290                 295                 300
```

```
Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
            325                 330                 335

Pro Leu Arg Glu Arg Arg Lys Arg Gly Leu Phe Gly Ala Ile Ala
        340                 345                 350

Gly Phe Ile Glu Gly Gly Trp Gln Gly Met Val Asp Gly Trp Tyr Gly
        355                 360                 365

Tyr His His Ser Asn Glu Gln Gly Ser Gly Tyr Ala Ala Asp Lys Glu
        370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
            420                 425                 430

Phe Leu Asp Val Trp Thr Tyr Asn Ala Glu Leu Leu Val Leu Met Glu
        435                 440                 445

Asn Glu Arg Thr Leu Asp Phe His Asp Ser Asn Val Lys Asn Leu Tyr
450                 455                 460

Asp Lys Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
                485                 490                 495

Val Arg Asn Gly Thr Tyr Asp Tyr Pro Gln Tyr Ser Glu Glu Ala Arg
            500                 505                 510

Leu Lys Arg Glu Glu Ile Ser Gly Val Lys Leu Glu Ser Ile Gly Thr
        515                 520                 525

Tyr Gln Ile Leu Ser Ile Tyr Ser Thr Val Ala Ser Ser Leu Ala Leu
530                 535                 540

Ala Ile Met Val Ala Gly Leu Ser Leu Trp Met Cys Ser Asn Gly Ser
545                 550                 555                 560

Leu Gln Cys Arg Ile Cys Ile
                565

<210> SEQ ID NO 3
<211> LENGTH: 1656
<212> TYPE: DNA
<213> ORGANISM: Influenza A virus
<220> FEATURE:
<221> NAME/KEY: CDS
<222> LOCATION: (1)..(1656)

<400> SEQUENCE: 3 gat cag att tgc att ggt tac cat gca aac aac tcg aca gag cag gtt      48
Asp Gln Ile Cys Ile Gly Tyr His Ala Asn Asn Ser Thr Glu Gln Val
1               5                   10                  15 gac aca ata atg gaa aag aac gtt act gtt aca cat gcc caa gac ata      96
Asp Thr Ile Met Glu Lys Asn Val Thr Val Thr His Ala Gln Asp Ile
                20                  25                  30 ctg gaa aag aca cac aac ggg aag ctc tgc gat cta gat gga gtg aag     144
Leu Glu Lys Thr His Asn Gly Lys Leu Cys Asp Leu Asp Gly Val Lys
            35                  40                  45 cct ctg att tta aga gat tgt agt gta gct gga tgg ctc ctc gga aac     192
Pro Leu Ile Leu Arg Asp Cys Ser Val Ala Gly Trp Leu Leu Gly Asn
        50                  55                  60 cca atg tgt gac gaa ttc atc aat gtg ccg gaa tgg tct tac ata gtg     240
```

```
                Pro Met Cys Asp Glu Phe Ile Asn Val Pro Glu Trp Ser Tyr Ile Val
                65              70                  75                  80 gag aag gcc aac cca gcc aat gac ctc tgt tac cca ggg aat ttc aac        288
Glu Lys Ala Asn Pro Ala Asn Asp Leu Cys Tyr Pro Gly Asn Phe Asn
                    85                  90                  95 gac tat gaa gaa ctg aaa cac cta ttg agc aga ata aac cat ttt gag        336
Asp Tyr Glu Glu Leu Lys His Leu Leu Ser Arg Ile Asn His Phe Glu
                100                 105                 110 aaa att cag atc atc ccc aaa agt tct tgg tcc gat cat gaa gcc tca        384
Lys Ile Gln Ile Ile Pro Lys Ser Ser Trp Ser Asp His Glu Ala Ser
                    115                 120                 125 tca ggg gtg agc tca gca tgt cca tac cag gga acg ccc tcc ttt ttc        432
Ser Gly Val Ser Ser Ala Cys Pro Tyr Gln Gly Thr Pro Ser Phe Phe
        130                 135                 140 aga aat gtg gta tgg ctt atc aaa aag aac aat aca tac cca aca ata        480
Arg Asn Val Val Trp Leu Ile Lys Lys Asn Asn Thr Tyr Pro Thr Ile
145                 150                 155                 160 aag aga agc tac aat aat acc aac cag gaa gat ctt ttg ata ctg tgg        528
Lys Arg Ser Tyr Asn Asn Thr Asn Gln Glu Asp Leu Leu Ile Leu Trp
                    165                 170                 175 ggg att cat cat tct aat gat gcg gca gag cag aca aag ctc tat caa        576
Gly Ile His His Ser Asn Asp Ala Ala Glu Gln Thr Lys Leu Tyr Gln
                180                 185                 190 aac cca acc acc tat att tcc gtt ggg aca tca aca cta aac cag aga        624
Asn Pro Thr Thr Tyr Ile Ser Val Gly Thr Ser Thr Leu Asn Gln Arg
                    195                 200                 205 ttg gta cca aaa ata gct act aga tcc aaa gta aac ggg caa agt gga        672
Leu Val Pro Lys Ile Ala Thr Arg Ser Lys Val Asn Gly Gln Ser Gly
        210                 215                 220 agg atg gat ttc ttc tgg aca att tta aaa ccg aat gat gca atc aac        720
Arg Met Asp Phe Phe Trp Thr Ile Leu Lys Pro Asn Asp Ala Ile Asn
225                 230                 235                 240 ttc gag agt aat gga aat ttc att gct cca gaa tat gca tac aaa att        768
Phe Glu Ser Asn Gly Asn Phe Ile Ala Pro Glu Tyr Ala Tyr Lys Ile
                    245                 250                 255 gtc aag aaa ggg gac tca gca att gtt aaa agt gaa gtg gaa tat ggt        816
Val Lys Lys Gly Asp Ser Ala Ile Val Lys Ser Glu Val Glu Tyr Gly
                260                 265                 270 aac tgc aac aca aag tgt caa act cca ata ggg gcg ata aac tct agt        864
Asn Cys Asn Thr Lys Cys Gln Thr Pro Ile Gly Ala Ile Asn Ser Ser
        275                 280                 285 atg cca ttc cac aac ata cac cct ctc acc atc ggg gaa tgc ccc aaa        912
Met Pro Phe His Asn Ile His Pro Leu Thr Ile Gly Glu Cys Pro Lys
        290                 295                 300 tat gtg aaa tca aac aaa tta gtc ctt gcg act ggg ctc aga aat agt        960
Tyr Val Lys Ser Asn Lys Leu Val Leu Ala Thr Gly Leu Arg Asn Ser
305                 310                 315                 320 cct cta aga gaa aga aga aga aaa aga gga cta ttt gga gct ata gca        1008
Pro Leu Arg Glu Arg Arg Arg Lys Arg Gly Leu Phe Gly Ala Ile Ala
                    325                 330                 335 ggg ttt ata gag gga gga tgg cag gga atg gta gat ggt tgg tat ggg        1056
Gly Phe Ile Glu Gly Gly Trp Gln Gly Met Val Asp Gly Trp Tyr Gly
                340                 345                 350 tac cac cat agc aat gag cag ggg agt ggg tac gct gca gac aaa gaa        1104
Tyr His His Ser Asn Glu Gln Gly Ser Gly Tyr Ala Ala Asp Lys Glu
        355                 360                 365 tcc act caa aag gca ata gat gga gtc acc aat aag gtc aac tcg atc        1152
Ser Thr Gln Lys Ala Ile Asp Gly Val Thr Asn Lys Val Asn Ser Ile
370                 375                 380
```

```
att gac aaa atg aac act cag ttt gag gcc gtt gga agg gaa ttt aat      1200
Ile Asp Lys Met Asn Thr Gln Phe Glu Ala Val Gly Arg Glu Phe Asn
385             390                 395                 400 aac tta gaa agg aga ata gag aat tta aac aag aaa atg gaa gac gga      1248
Asn Leu Glu Arg Arg Ile Glu Asn Leu Asn Lys Lys Met Glu Asp Gly
                405                 410                 415 ttc cta gat gtc tgg act tat aat gct gaa ctt ctg gtt ctc atg gaa     1296
Phe Leu Asp Val Trp Thr Tyr Asn Ala Glu Leu Leu Val Leu Met Glu
        420                 425                 430 aat gag aga act cta gac ttc cat gat tca aat gtc aag aac ctt tac     1344
Asn Glu Arg Thr Leu Asp Phe His Asp Ser Asn Val Lys Asn Leu Tyr
    435                 440                 445 gac aag gtc cga cta cag ctt agg gat aat gca aag gag ctg ggt aac     1392
Asp Lys Val Arg Leu Gln Leu Arg Asp Asn Ala Lys Glu Leu Gly Asn
450                 455                 460 ggt tgt ttc gag ttc tat cac aaa tgt gat aat gaa tgt atg gaa agt     1440
Gly Cys Phe Glu Phe Tyr His Lys Cys Asp Asn Glu Cys Met Glu Ser
465             470                 475                 480 gta aga aac gga acg tat gac tac ccg cag tat tca gaa gaa gca aga     1488
Val Arg Asn Gly Thr Tyr Asp Tyr Pro Gln Tyr Ser Glu Glu Ala Arg
                485                 490                 495 tta aaa aga gag gaa ata agt gga gta aaa ttg gaa tca ata gga act     1536
Leu Lys Arg Glu Glu Ile Ser Gly Val Lys Leu Glu Ser Ile Gly Thr
        500                 505                 510 tac caa ata ctg tca att tat tca aca gtt gcg agt tct cta gca ctg     1584
Tyr Gln Ile Leu Ser Ile Tyr Ser Thr Val Ala Ser Ser Leu Ala Leu
    515                 520                 525 gca atc atg gtg gct ggt cta tct ttg tgg atg tgc tcc aat ggg tcg     1632
Ala Ile Met Val Ala Gly Leu Ser Leu Trp Met Cys Ser Asn Gly Ser
530                 535                 540 tta caa tgc aga att tgc att taa                                     1656
Leu Gln Cys Arg Ile Cys Ile
545             550

<210> SEQ ID NO 4
<211> LENGTH: 551
<212> TYPE: PRT
<213> ORGANISM: Influenza A virus

<400> SEQUENCE: 4

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Asn Pro Ala Asn Asp Leu Cys Tyr Pro Gly Asn Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asp His Glu Ala Ser
        115                 120                 125

Ser Gly Val Ser Ser Ala Cys Pro Tyr Gln Gly Thr Pro Ser Phe Phe
    130                 135                 140
```

```
Arg Asn Val Val Trp Leu Ile Lys Lys Asn Thr Tyr Pro Thr Ile
145                 150                 155                 160

Lys Arg Ser Tyr Asn Asn Thr Asn Gln Glu Asp Leu Leu Ile Leu Trp
                165                 170                 175

Gly Ile His His Ser Asn Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
            195                 200                 205

Leu Val Pro Lys Ile Ala Thr Arg Ser Lys Val Asn Gly Gln Ser Gly
        210                 215                 220

Arg Met Asp Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Val Lys Ser Glu Val Glu Tyr Gly
            260                 265                 270

Asn Cys Asn Thr Lys Cys Gln Thr Pro Ile Gly Ala Ile Asn Ser Ser
            275                 280                 285

Met Pro Phe His Asn Ile His Pro Leu Thr Ile Gly Glu Cys Pro Lys
290                 295                 300

Tyr Val Lys Ser Asn Lys Leu Val Leu Ala Thr Gly Leu Arg Asn Ser
305                 310                 315                 320

Pro Leu Arg Glu Arg Arg Lys Arg Gly Leu Phe Gly Ala Ile Ala
                325                 330                 335

Gly Phe Ile Glu Gly Gly Trp Gln Gly Met Val Asp Gly Trp Tyr Gly
            340                 345                 350

Tyr His His Ser Asn Glu Gln Gly Ser Gly Tyr Ala Ala Asp Lys Glu
            355                 360                 365

Ser Thr Gln Lys Ala Ile Asp Gly Val Thr Asn Lys Val Asn Ser Ile
        370                 375                 380

Ile Asp Lys Met Asn Thr Gln Phe Glu Ala Val Gly Arg Glu Phe Asn
385                 390                 395                 400

Asn Leu Glu Arg Arg Ile Glu Asn Leu Asn Lys Lys Met Glu Asp Gly
                405                 410                 415

Phe Leu Asp Val Trp Thr Tyr Asn Ala Glu Leu Leu Val Leu Met Glu
            420                 425                 430

Asn Glu Arg Thr Leu Asp Phe His Asp Ser Asn Val Lys Asn Leu Tyr
            435                 440                 445

Asp Lys Val Arg Leu Gln Leu Arg Asp Asn Ala Lys Glu Leu Gly Asn
450                 455                 460

Gly Cys Phe Glu Phe Tyr His Lys Cys Asp Asn Glu Cys Met Glu Ser
465                 470                 475                 480

Val Arg Asn Gly Thr Tyr Asp Tyr Pro Gln Tyr Ser Glu Glu Ala Arg
                485                 490                 495

Leu Lys Arg Glu Glu Ile Ser Gly Val Lys Leu Glu Ser Ile Gly Thr
            500                 505                 510

Tyr Gln Ile Leu Ser Ile Tyr Ser Thr Val Ala Ser Ser Leu Ala Leu
            515                 520                 525

Ala Ile Met Val Ala Gly Leu Ser Leu Trp Met Cys Ser Asn Gly Ser
530                 535                 540

Leu Gln Cys Arg Ile Cys Ile
545                 550
```

MONOCLONAL ANTIBODIES TARGETING NEUTRALIZING EPITOPES ON H5 INFLUENZA VIRUS OF CLADE 2.3

CROSS-REFERENCE OF THE RELATED APPLICATION

The present application is a 35 U.S.C. §371 National Phase Entry Application of PCT/SG2012/000012, filed 12 Jan. 2012, and designating the United States, which is incorporated herein by reference.

SEQUENCE SUBMISSION

The present application is being filed along with a Sequence Listing in electronic format. The Sequence Listing is entitled 2577210PCTSequenceListing.txt, created on 10 Jan. 2012 and is 26 kb in size. The information in the electronic format of the Sequence Listing is incorporated herein by reference in its entirety.

BACKGROUND OF THE INVENTION

The present invention relates to the murine monoclonal antibodies C, F and H specific to a major neutralizing epitope of influenza H5 hemagglutinin of clade 2.3 and active fragments thereof. The present invention also relates to methods and compositions for the prophylaxis and treatment of H5N1 influenza using murine monoclonal antibodies C, F or H or active fragments thereof. The present invention additionally relates to methods and compositions for providing universal protection against H5 influenza viruses using murine monoclonal antibodies C, F or H or fragments thereof together with a complementary murine monoclonal antibody or active fragments thereof. The present invention further relates to methods and compositions for the characterization and quantification of H5 expression using these murine monoclonal antibody or fragments thereof.

The publications and other materials used herein to illuminate the background of the invention or provide additional details respecting the practice, are incorporated by reference, and for convenience are respectively grouped in the Bibliography.

The recent emergence of H5N1 strains of influenza A virus and the high mortality caused by them in humans has raised concerns for the possibility of a future influenza pandemic. Preventive and therapeutic measures against circulating H5N1 strains have received a lot of interest and effort globally to prevent another pandemic outbreak. Present vaccine strategies have been hindered by antigenic variation of the influenza strains. Present vaccine strategies requiring endogenous synthesis of antibodies will not provide immediate protection against H5N1 infections in the event of a pandemic. Currently licensed antiviral drugs include the M2 ion-channel inhibitors (rimantidine and amantidine) and the neuraminidase inhibitors (oseltamivir and zanamivir). The H5N1 viruses are known to be resistant to the M2 ion-channel inhibitors (Biegel et al., 2005). Newer strains of H5N1 viruses are being isolated which are also resistant to the neuraminidase inhibitors, i.e, oseltamivir and zanamivir (Le et al., 2008; de Jong et al., 2005). The neuraminidase inhibitors also require high doses and prolonged treatment (de Jong and Hien, 2006), increasing the likelihood of unwanted side effects. Hence, alternative strategies for treatment of influenza are warranted.

Passive immunotherapy using monoclonal antibodies has been viewed as a viable option for treatment of many infectious diseases. Currently, there has been a lot of focus on therapeutic approaches using neutralizing antibodies against the HA1 protein of the influenza virus. This protein is easy to target as it is on the surface of the virus and antibodies against this protein can neutralize the virus efficiently. Hence, monoclonal antibodies (Mabs) against neutralizing epitopes of H5 hemagglutinin (HA) may be an attractive alternative to active vaccination of humans, in particular for those individuals who are at high risk from influenza infection, viz. the immuno-compromised patients or the elderly who do not respond well to active immunization. It is important that any Mab product should offer broad protection against circulating strains of H5N1 influenza and should prevent the selection of neutralization escape mutants in vivo. One technique to increase protection against circulating strains of H5N1 influenza and to prevent escape mutants is a combination therapy using complementary Mabs (Prabakaran et al., 2009).

It is desired to identify monoclonal antibodies that target major neutralizing epitopes of influenza H5 hemagglutinin of clade 2.3. It is also desired to identify monoclonal antibodies that can be used for the prophylaxis and treatment of H5N1 influenza. It is further desired to identify monoclonal antibodies that can be used to provide universal protection against H5 influenza viruses. It is also desired to identify monoclonal antibodies that can be used for the identification, characterization and/or quantification of H5 expression.

SUMMARY OF THE INVENTION

The present invention relates to murine monoclonal antibodies C, F and H which target major neutralizing epitopes of influenza H5 hemagglutinin of clade 2.3 and active fragments thereof. The present invention also relates to methods and compositions for the prophylaxis and treatment of H5N1 influenza using murine monoclonal antibodies C, F or H or active fragments thereof. The present invention additionally relates to methods and compositions for providing universal protection against H5 influenza viruses using murine monoclonal antibodies C, F or H or fragments thereof together with a complementary murine monoclonal antibody or active fragments thereof. The present invention further relates to methods and compositions for the characterization and quantification of H5 expression using these murine monoclonal antibody or fragments thereof.

Thus, in a first aspect, the present invention provides a monoclonal antibody specific to a major neutralizing epitope of influenza H5 hemagglutinin and active fragments thereof, i.e., antigen binding fragments (also referred to herein as antibody fragments). In some embodiments, the monoclonal antibody or fragment thereof specifically binds to a conformational epitope of H5 hemagglutinin (HA), wherein the conformational epitope is comprised of amino acids 152Lys, 184Ala and 194Pro of the mature HA protein. In another embodiment, the monoclonal antibody or fragment thereof specifically binds to a conformational epitope of H5 hemagglutinin to which murine monoclonal antibody C specifically binds. In an additional embodiment, the monoclonal antibody is murine monoclonal antibody C. In a further embodiment, the monoclonal antibody is murine monoclonal antibody C produced by murine hybridoma C.

In other embodiments, the monoclonal antibody or fragment thereof specifically binds to a conformational epitope of H5 hemagglutinin (HA), wherein the conformational epitope is comprised of amino acids 152Lys and 221Gly of the mature HA protein. In another embodiment, the monoclonal antibody or fragment thereof specifically binds to a conformational epitope of 1-15 hemagglutinin to which murine monoclonal antibody F specifically binds. In an additional embodiment, the monoclonal antibody is murine monoclonal antibody F. In a further embodiment, the monoclonal antibody is murine monoclonal antibody F produced by murine hybridoma F.

In further embodiments, the monoclonal antibody or fragment thereof specifically binds to a conformational epitope of H5 hemagglutinin (HA), wherein the conformational epitope is comprised of amino acids 141Pro and 152Lys of the mature HA protein. In another embodiment, the monoclonal antibody or fragment thereof specifically binds to a conformational epitope of H5 hemagglutinin to which murine monoclonal antibody H specifically binds. In an additional embodiment, the monoclonal antibody is murine monoclonal antibody H. In a further embodiment, the monoclonal antibody is murine monoclonal antibody H produced by murine hybridoma H.

In another embodiment, the present invention provides a nucleic acid encoding a monoclonal antibody or antigen binding fragment thereof described herein. In one embodiment the nucleic acid encodes the murine monoclonal antibody C or antigen binding fragment thereof. In another embodiment the nucleic acid encodes the murine monoclonal antibody F or antigen binding fragment thereof. In a further embodiment the nucleic acid encodes the murine monoclonal antibody H or antigen binding fragment thereof. In one embodiment, the present invention provides a vector comprising the nucleic acid. In another embodiment, the present invention proves a cell comprising and expressing the vector.

In a second aspect, the present invention provides methods and compositions for the prophylaxis and treatment of H5N1 influenza using a murine monoclonal antibody or fragments thereof described herein. In one embodiment, the present invention provides a pharmaceutical composition comprising a monoclonal antibody described herein and a pharmaceutically acceptable diluent or carrier. In some embodiments, the monoclonal antibody is murine monoclonal antibody C. In other embodiments, the monoclonal antibody is murine monoclonal antibody F. In further embodiments, the monoclonal antibody is murine monoclonal antibody H. In another embodiment, the pharmaceutical composition comprises an antigen binding fragment of a monoclonal antibody described herein and a pharmaceutically acceptable diluent or carrier. In some embodiments, the antigen binding fragment is an antigen binding fragment of murine monoclonal antibody C. In other embodiments, the antigen binding fragment is an antigen binding fragment of murine monoclonal antibody F. In further embodiments, the antigen binding fragment is an antigen binding fragment of monoclonal antibody H. In an additional embodiment, the pharmaceutical composition comprises a nucleic acid molecule encoding said antibody or antibody fragment and a pharmaceutically acceptable diluent or carrier. In a further embodiment, the pharmaceutical composition comprises a vector comprising said nucleic acid and a pharmaceutically acceptable diluent or carrier. In another embodiment, the pharmaceutical composition comprises a cell expressing said vector and a pharmaceutically acceptable diluent or carrier. In an additional embodiment, the pharmaceutical composition comprises a nucleic acid molecule encoding said antibody or antibody fragment and a pharmaceutically acceptable diluent or carrier. In a further embodiment, the pharmaceutical composition comprises a vector comprising said nucleic acid and a pharmaceutically acceptable diluent or carrier. In another embodiment, the pharmaceutical composition comprises a cell expressing said vector and a pharmaceutically acceptable diluent or carrier.

In one embodiment, the present invention provides a method of reducing influenza H5N1 virus infection in a subject, or lowering the risk of influenza H5N1 virus infection in a subject, inhibiting infection of a subject by one or more influenza H5N1 virus strains or isolates of clade 2.3, or prophylaxis of influenza infection or disease by one or more influenza H5N1 virus strains or isolates of clade 2.3. In this embodiment, the method comprises administering to a subject in need thereof, a therapeutically effective amount of a monoclonal antibody or an antigen binding fragment thereof described herein, a nucleic acid molecule comprising a polynucleotide encoding said antibody or antibody fragment; a vector comprising said polynucleotide; or a cell expressing said vector. In one embodiment, the monoclonal antibody is murine monoclonal antibody C. In another embodiment, the monoclonal antibody is murine monoclonal antibody F. In a further embodiment, the monoclonal antibody is murine monoclonal antibody H. In one embodiment, the subject is immunocompromised, is an infant, is a young child or is elderly. In another embodiment, administration provides a therapeutic benefit. In an additional embodiment, therapeutic benefit comprises inhibiting increases in influenza virus titer, decreasing influenza virus titer, inhibiting increases in influenza virus replication, decreasing influenza virus replication, inhibiting increases in influenza virus proliferation or decreasing influenza virus proliferation, or decreasing progression, severity, frequency, duration or probability one or more symptoms or complications associated with influenza virus infection in a subject. In one embodiment, a symptom or complication is selected from chills, fever, cough, sore throat, nasal congestion, sinus congestion, nasal infection, sinus infection, body ache, head ache, fatigue, pneumonia, bronchitis, ear infection, ear ache and death. In another embodiment, the therapeutic benefit comprises hastening a subject's recovery from influenza H5N1 virus infection. In a further embodiment, the agent that is administered to the subject is administered prior to, substantially contemporaneously with or following influenza H5N1 virus infection of the subject.

In one embodiment, the methods and compositions for the prophylaxis and treatment of H5N1 influenza uses a murine monoclonal antibody or fragments thereof described herein in combination with at least one complementary monoclonal antibody or antibody fragment thereof. According to this embodiment, the use of the complementary Mabs increases protection against circulating strains of influenza H5N1 virus and to prevent escape mutants. In some embodiments, the methods and compositions use a first murine monoclonal antibody or active fragments thereof described herein in combination with a second complementary murine monoclonal antibody or active fragments thereof. In one embodiment, the first murine monoclonal antibody is monoclonal antibody C. In another embodiment, the first murine monoclonal antibody is monoclonal antibody F. In a further embodiment, the first murine monoclonal antibody is monoclonal antibody H. In one embodiment the second complementary murine monoclonal antibody is murine monoclonal antibody 2D9. The compositions and methods are as described herein with respect to the use of a single monoclonal antibody or fragment thereof except that the complementary monoclonal antibodies or fragments thereof are used in the methods and compositions.

In a third aspect, the present invention provides methods and compositions for the characterization and/or quantification of H5 expression in a sample using a monoclonal antibody or fragments thereof described herein. In some embodiments, the monoclonal antibody is murine monoclonal antibody C. In other embodiments, the monoclonal antibody is murine monoclonal antibody F. In further embodiments, the monoclonal antibody is murine monoclonal antibody H.

In one embodiment, the H5 expression relates to the expression of HA of influenza H5N1 viruses. In one embodiment, the composition comprises a monoclonal antibody or fragments thereof described herein. In some embodiments, the monoclonal antibody is murine monoclonal antibody C. In other embodiments, the monoclonal antibody is murine monoclonal antibody F. In further embodiments, the monoclonal antibody is murine monoclonal antibody H. In another embodiment, the method comprises detecting the binding of the H5 with a monoclonal antibody or fragments thereof described herein. In some embodiments, the monoclonal antibody is murine monoclonal antibody C. In other embodiments, the monoclonal antibody is murine monoclonal antibody F. In further embodiments, the monoclonal antibody is murine monoclonal antibody H. In one embodiment, the invention relates to immunofluorescence assays (IFA), immunohistochemical assays and other methods that utilize such binding proteins, including ELISA, hemagglutination inhibition (HI) assays and virus neutralization (VN) assays.

In a fourth aspect, the present invention provides kits and methods for the detection of an influenza A virus in a biological specimen. In one embodiment, the detection relates to the detection of influenza H5N1 viruses. In another embodiment, the detection relates to the detection of influenza H5N1 viruses of the clade 2 family. In a further embodiment, the detection relates to the detection of influenza H5N1 viruses of clade 2.3. In one embodiment, the method comprises contacting the specimen with a first antibody which is a monoclonal antibody or antibody fragment thereof described herein. In some embodiments, the monoclonal antibody is murine monoclonal antibody C. In other embodiments, the monoclonal antibody is murine monoclonal antibody F. In further embodiments, the monoclonal antibody is murine monoclonal antibody H. In another embodiment, the method further comprises contacting the specimen with a second antibody that specifically binds to an epitope of H5 hemagglutinin of an influenza A virus in which the second antibody contains or is conjugated to a detectable element. In some embodiments, the second antibody contains a radioactive atom, is conjugated to a fluorescent molecule, or is conjugated to an enzyme. In other embodiments, the first antibody is immobilized on a solid surface.

In one embodiment, the kit comprises a first antibody which is a monoclonal antibody or antibody fragment thereof described herein together with instructions for performing an assay to detect the influenza A virus. In one embodiment, the kit relates to the detection of influenza H5N1 viruses. In another embodiment, the kit relates to the detection of influenza H5N1 viruses of the clade 2 family. In a further embodiment, the kit relates to the detection of influenza H5N1 viruses of clade 2.3. In some embodiments, the monoclonal antibody is murine monoclonal antibody C. In other embodiments, the monoclonal antibody is murine monoclonal antibody F. In further embodiments, the monoclonal antibody is murine monoclonal antibody H. In another embodiment, the kit further comprises a second antibody that specifically binds to an epitope of H5 hemagglutinin of an influenza A virus in which the second antibody contains or is conjugated to a detectable element. In some embodiments, the second antibody contains a radioactive atom, is conjugated to a fluorescent molecule, or is conjugated to an enzyme. In other embodiments, the first antibody is immobilized on a solid surface.

BRIEF DESCRIPTION OF THE FIGURE

FIG. 1 shows the reactivity against H5 strain with either mAb C, F or H in Anhui H5 infected MDCK cells with IFA. Infected and fixed cells were stained with either of the Mabs or PBS and secondary antibody anti-mouse FITC.

DETAILED DESCRIPTION OF THE INVENTION

The present invention relates to murine monoclonal antibodies C, F and H which target major neutralizing epitopes of influenza H5 hemagglutinin of clade 2.3 and active fragments thereof. The present invention also relates to methods and compositions for the prophylaxis and treatment of H5N1 influenza using murine monoclonal antibodies C, F or H or active fragments thereof. The present invention additionally relates to methods and compositions for providing universal protection against H5 influenza viruses using murine monoclonal antibodies C, F or H or fragments thereof together with murine monoclonal antibody 2D9 or active fragments thereof. The present invention further relates to methods and compositions for the characterization and quantification of H5 expression using these murine monoclonal antibody or fragments thereof.

By "isolated" is meant a biological molecule free from at least some of the components with which it naturally occurs.

The terms "antibody" or "antibodies" as used herein are art-recognized terms and are understood to refer to molecules or active fragments of molecules that bind to known antigens, particularly to immunoglobulin molecules and to immunologically active portions of immunoglobulin molecules, i.e., molecules that contain a binding site that specifically binds an antigen. An immunoglobulin is a protein comprising one or more polypeptides substantially encoded by the immunoglobulin kappa and lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Also subclasses of the heavy chain are known. For example, IgG heavy chains in humans can be any of IgG1, IgG2, IgG3 and IgG4 subclass. The immunoglobulin according to the invention can be of any class (IgG, IgM, IgD, IgE, IgA and IgY) or subclass (IgG1, IgG2, IgG3, IgG4, IgA1 and IgA2) of immunoglobulin molecule.

As used herein "specifically binds" in reference to an antibody means that the antibody binds to its target antigen with greater affinity that it does to a structurally different antigen(s).

A typical immunoglobulin structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as full length intact antibodies or as a number of well-characterized fragments produced by digestion with various peptidases or chemicals. Thus, for example, pepsin digests an antibody below the disulfide linkages in the hinge region to produce $F(ab')_2$, a dimer of Fab which itself is a light chain joined to $V_H$-$CH_1$ by a disulfide bond. The $F(ab')_2$ may be reduced under mild conditions to break the disulfide linkage in the hinge region thereby converting the $F(ab')_2$ dimer into an Fab' monomer. The Fab' monomer is essentially a Fab fragment with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that any of a variety of antibody fragments may be synthesized de novo either chemically or by utilizing recombinant DNA methodology. Thus, the term antibody, as used herein also includes antibody fragments either produced by the modification of whole antibodies or synthesized de novo or antibodies and fragments obtained by using recombinant DNA methodologies.

"Antibodies" are intended within the scope of the present invention to include chimeric or humanized monoclonal antibodies, as well as active fragments thereof. Examples of active fragments of molecules that bind to known antigens include separated light and heavy chains, Fab, Fab/c, Fv, Fab', and F(ab)$_2$ fragments, including the products of an Fab immunoglobulin expression library and epitope-binding fragments of any of the antibodies and fragments mentioned above.

These active fragments can be derived from an antibody of the present invention by a number of techniques. For example, monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw et al. (1982); Rousseaux et al. (1986).

Recombinantly made antibodies may be conventional full length antibodies, active antibody fragments known from proteolytic digestion, unique active antibody fragments such as Fv or single chain Fv (scFv), domain deleted antibodies, and the like. An Fv antibody is about 50 Kd in size and comprises the variable regions of the light and heavy chain. A single chain Fv ("scFv") polypeptide is a covalently linked VH::VL heterodimer which may be expressed from a nucleic acid including VH- and VL-encoding sequences either joined directly or joined by a peptide-encoding linker. See Huston et al. (1988). A number of structures for converting the naturally aggregated, but chemically separated light and heavy polypeptide chains from an antibody V region into an scFv molecule which will fold into a three dimensional structure substantially similar to the structure of an antigen-binding site. See, e.g. U.S. Pat. Nos. 5,091,513; 5,132,405 and 4,956,778.

The combining site refers to the part of an antibody molecule that participates in antigen binding. The antigen binding site is formed by amino acid residues of the N-terminal variable ("V") regions of the heavy ("H") and light ("L") chains. The antibody variable regions comprise three highly divergent stretches referred to as "hypervariable regions" or "complementarity determining regions" (CDRs) which are interposed between more conserved flanking stretches known as "framework regions" (FRs). In an antibody molecule, the three hypervariable regions of a light chain (LCDR1, LCDR2, and LCDR3) and the three hypervariable regions of a heavy chain (HCDR1, HCDR2 and HCDR3) are disposed relative to each other in three dimensional space to form an antigen binding surface or pocket. The antibody combining site therefore represents the amino acids that make up the CDRs of an antibody and any framework residues that make up the binding site pocket.

The identity of the amino acid residues in a particular antibody that make up the combining site can be determined using methods well known in the art. See, e.g., U.S. Patent Application Publication No. 2010/0080800. The identity of the amino acid residues in a particular antibody that are outside the CDRs, but nonetheless make up part of the combining site by having a side chain that is part of the lining of the combining site (i.e., it is available to linkage through the combining site), can be determined using methods well known in the art such as molecular modeling and X-ray crystallography. See e.g., Riechmann et al. (1988).

Chimeric antibodies are those in which one or more regions of the antibody are from one species of animal and one or more regions of the antibody are from a different species of animal. A preferred chimeric antibody is one which includes regions from a primate immunoglobulin. A chimeric antibody for human clinical use is typically understood to have variable regions from a non-human animal, e.g. a rodent, with the constant regions from a human. In contrast, a humanized antibody uses CDRs from the non-human antibody with most or all of the variable framework regions from and all the constant regions from a human immunoglobulin. A human chimeric antibody is typically understood to have the variable regions from a rodent. A typical human chimeric antibody has human heavy constant regions and human light chain constant regions with the variable regions of both the heavy and light coming from a rodent antibody. A chimeric antibody may include some changes to a native amino acid sequence of the human constant regions and the native rodent variable region sequence. Chimeric and humanized antibodies may be prepared by methods well known in the art including CDR grafting approaches (see, e.g., U.S. Pat. Nos. 5,843,708; 6,180,370; 5,693,762; 5,585,089; 5,530,101), chain shuffling strategies (see e.g., U.S. Pat. No. 5,565,332; Rader et al. (1998)), molecular modeling strategies (U.S. Pat. No. 5,639,641), and the like.

A "humanized antibody" as used herein in the case of a two chain antibody is one where at least one chain is humanized. A humanized antibody chain has a variable region where one or more of the framework regions are human. A humanized antibody which is a single chain is one where the chain has a variable region where one or more of the framework regions are human. The non-human portions of the variable region of the humanized antibody chain or fragment thereof is derived from a non-human source, particularly a non-human antibody, typically of rodent origin. The non-human contribution to the humanized antibody is typically provided in form at least one CDR region which is interspersed among framework regions derived from one (or more) human immunoglobulin(s). In addition, framework support residues may be altered to preserve binding affinity.

The humanized antibody may further comprise constant regions (e.g., at least one constant region or portion thereof, in the case of a light chain, and preferably three constant regions in the case of a heavy chain). The constant regions of a humanized antibody if present generally are human. Methods to obtain "humanized antibodies" are well known to those skilled in the art. See, e.g., U.S. Patent Application Publication No. 2010/0080800.

The term constant region (CR) as used herein refers to constant regions genes of the immunoglobulin. The constant region genes encode the portion of the antibody molecule which confers effector functions. For Chimeric human antibodies and humanized antibodies, typically non-human (e.g., murine), constant regions are substituted by human constant regions. The constant regions of the subject chimeric or humanized antibodies are typically derived from human immunoglobulins. The heavy chain constant region can be selected from any of the five isotypes: alpha, delta, epsilon, gamma or mu. Further, heavy chains of various subclasses (such as the IgG subclasses of heavy chains) are responsible for different effector functions and thus, by choosing the desired heavy chain constant region, antibodies with desired effector function can be produced. Constant regions that may be used within the scope of this invention are gamma 1 (IgG1), particularly an Fc region of the gamma 1 (IgG1) isotype, gamma 3 (IgG3) and especially gamma 4 (IgG4). The light chain constant region can be of the kappa or lambda type, preferably the kappa type. In one embodiment the light chain constant region is the human kappa constant chain (Hieter et al. (1980)) and the heavy constant chain is the human IgG4 constant chain.

The term variable region (VR) as used herein refers to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

The term framework region (FR) as used herein refers to one or more of the framework regions within the variable regions of the light and heavy chains of an antibody (See Kabat et al. (1992); Johnson and Wu (2001); http colon backslash backslash immuno dot bme dot nwa dot edu). These expressions include those amino acid sequences regions interposed between the CDRs within the variable regions of the light and heavy chains of an antibody.

CDR and FR residues are determined according to a standard sequence definition (Kabat et al. (1992), and a structural definition (e.g., as in Chothia and Lesk (1987)). Where these two methods result in slightly different identifications of a CDR, the structural definition is preferred, but the residues identified by the sequence definition method are considered important FR residues for determining which framework residues to import into a consensus sequence.

The term "monoclonal antibody" is also well recognized in the art and refers to an antibody that is the product of a single cloned antibody producing cell. Monoclonal antibodies are typically made by fusing a normally short-lived, antibody-producing B cell to a fast-growing cell, such as a cancer cell (sometimes referred to as an "immortal" cell). The resulting hybrid cell, or hybridoma, multiplies rapidly, creating a clone that produces the antibody.

The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab)$_2$, Fabc and/or Fv fragments. The term "antigen-binding fragment" refers to a polypeptide fragment of an immunoglobulin or antibody that binds antigen or competes with intact antibody (i.e., with the intact antibody from which they were derived) for antigen binding (i.e., specific binding). Binding fragments are produced by recombinant DNA techniques, or by enzymatic or chemical cleavage of intact immunoglobulins. Binding fragments include Fab, Fab', F(ab').sub.2, Fabc, Fv, single chains, and single-chain antibodies.

Humanized antibody of reduced immunogenicity refers to a humanized antibody exhibiting reduced immunogenicity relative to the parent antibody, e.g., the murine antibody.

Humanized antibody substantially retaining the binding properties of the parent antibody refers to a humanized antibody which retains the ability to specifically bind the antigen recognized by the parent antibody used to produce such humanized antibody. Preferably the humanized antibody will exhibit the same or substantially the same antigen-binding affinity and avidity as the parent antibody. Ideally, the affinity of the antibody will not be less than 10% of the parent antibody affinity, more preferably not less than about 30%, and most preferably the affinity will not be less than 50% of the parent antibody. Methods for assaying antigen-binding affinity are well known in the art and include half-maximal binding assays, competition assays, and Scatchard analysis.

The term "complementary monoclonal antibodies" refers to monoclonal antibodies in which one Mab interacts with a part of a particular antigen while the other Mab can interact with the rest or more than the rest of the particular antigen. The complementary pair serves as universal reagents for the particular antigen, such as H5N1, in either diagnosis or therapeutics. The active fields of the two Mabs may have overlapping region, but are not identical. An example of complementary anti-H5 monoclonal antibody is described by Prabakaran et al. (2009). Another example of complementary anti-H5 monoclonal antibody is described by He et al. (2010).

Further, the term "therapeutically effective amount" refers to the amount of antibody which, when administered to a human or animal, which is sufficient to result in a therapeutic effect in said human or animal. The effective amount is readily determined by one of skill in the art following routine procedures.

As used herein, the terms "treat," "prevent," "preventing," and "prevention" refer to the prevention of the recurrence or onset of one or more symptoms of a disorder in a subject resulting from the administration of a prophylactic or therapeutic agent.

The present application describes the characterization of a panel of neutralizing Mabs against H5 of clade 2.3 for their respective epitopes by epitope mapping. The present application also describes the evaluation of the therapeutic efficacies of these Mabs in hemagglutination inhibition and virus neutralization. The present application further describes the determination of the universal therapeutic efficacy of these Mabs together with Mab 2D9 against H5N1 viruses from different clades. Prior to the present invention, Mabs that were currently available had low neutralizing titers against H5 influenze viruses of clade 2.3. This problem of low neutralizing titers against H5 influenze viruses of clade 2.3 by the prior Mabs is solved by the Mabs of the present invention, i.e., Mabs C, F and H, which have high neutralizing titers against H5 influenze viruses of clade 2.3. These Mabs have an efficient reaction with H5 influenza virus of clade 2.3 in IFA, ELISA, HI and virus neutralization. In view of their efficient neutralization of H5 influenza virus of clade 2.3 and several other clades, the Mabs of the present invention can make up part of a universal therapeutic pair of monoclonal antibodies, which provides better protection than prior universal therapeutic Mab pairs. In addition, the Mabs of the present invention target new neutralizing epitopes on H5 virus of clade 2.3. As shown herein, Mabs C, F and H each show higher reactivity than Mab 2D9 to influenza H5N1 viruses of clade 2.3 and Mabs C, F and H each show higher reactivity to influenza H5N1 viruses of clade 2.3 than to other clades. In view of these characteristics of Mabs C, F and H, a major use of each of these three Mabs is to form a complementary Mab pair with 2D9 for universal detection or therapeutics.

In a first aspect, the present invention provides monoclonal antibodies specific to a major neutralizing epitope of influenza H5 hemagglutinin and active fragments thereof, i.e., antigen binding fragments (also referred to herein as antibody fragments). In some embodiments, the monoclonal antibody or fragment thereof specifically binds to a conformational epitope of H5 hemagglutinin (HA), wherein the conformational epitope is comprised of amino acids 152Lys, 184Ala and 194Pro of the mature HA protein. In another embodiment, the monoclonal antibody or fragment thereof specifically binds to a conformational epitope of H5 hemagglutinin to which murine monoclonal antibody C specifically binds. In an additional embodiment, the monoclonal antibody is a murine monoclonal antibody C. In a further embodiment, the monoclonal antibody is murine monoclonal antibody C produced by murine hybridoma C. Murine hybridoma C was deposited on 16 Nov. 2011 under terms of the Budapest Treaty with the CellBank Australia, 214 Hawkesbury Road, Westmead NSW 2145, Australia, and assigned Accession Number CBA20110011. The present invention also pertains to the murine hybridoma producing the murine monoclonal antibody C. In another embodiment, the monoclonal antibody is a chimeric or humanized monoclonal antibody. In particular, the chimeric or humanized monoclonal antibody specifically binds to a conformational epitope of H5 hemagglutinin to which murine monoclonal antibody C specifically binds. In one embodiment, a monoclonal antibody (either a murine monoclonal antibody or a chimeric or humanized monoclonal antibody) or fragment thereof specifically binds to a conformational epitope of H5 hemagglutinin (HA), wherein the conformational epitope is comprised of amino acids 152Lys, 184Ala and 194Pro of the mature HA protein.

In other embodiments, the monoclonal antibody or fragment thereof specifically binds to a conformational epitope of H5 hemagglutinin (HA), wherein the conformational epitope is comprised of amino acids 152Lys and 221Gly of the mature HA protein. In another embodiment, the monoclonal antibody or fragment thereof specifically binds to a conformational epitope of H5 hemagglutinin to which murine monoclonal antibody F specifically binds. In an additional embodiment, the monoclonal antibody is murine monoclonal antibody F. In a further embodiment, the monoclonal antibody is murine monoclonal antibody F produced by murine hybridoma F. Murine hybridoma F was deposited on 16 Nov. 2011 under terms of the Budapest Treaty with the CellBank Australia, 214 Hawkesbury Road, Westmead NSW 2145, Australia, and assigned Accession Number CBA20110012. The present invention also pertains to the murine hybridoma producing the murine monoclonal antibody F. In another embodiment, the monoclonal antibody is a chimeric or humanized monoclonal antibody. In particular, the chimeric or humanized monoclonal antibody specifically binds to a conformational epitope of H5 hemagglutinin to which murine monoclonal antibody F specifically binds. In one embodiment, a monoclonal antibody (either a murine monoclonal antibody or a chimeric or humanized monoclonal antibody) or fragment thereof specifically binds to a conformational epitope of H5 hemagglutinin (HA), wherein the conformational epitope is comprised of amino acids 152Lys and 221Gly of the mature HA protein.

In further embodiments, the monoclonal antibody or fragment thereof specifically binds to a conformational epitope of H5 hemagglutinin (HA), wherein the conformational epitope is comprised of amino acids 141Pro and 152Lys of the mature HA protein. In another embodiment, the monoclonal antibody or fragment thereof specifically binds to a conformational epitope of H5 hemagglutinin to which murine monoclonal antibody H specifically binds. In an additional embodiment, the monoclonal antibody is murine monoclonal antibody H. In a further embodiment, the monoclonal antibody is murine monoclonal antibody H produced by murine hybridoma H. Murine hybridoma H was deposited on 16 Nov. 2011 under terms of the Budapest Treaty with the CellBank Australia, 214 Hawkesbury Road, Westmead NSW 2145, Australia, and assigned Accession Number CBA20110013. The present invention also pertains to the murine hybridoma producing the murine monoclonal antibody H. In another embodiment, the monoclonal antibody is a chimeric or humanized monoclonal antibody. In particular, the chimeric or humanized monoclonal antibody specifically binds to a conformational epitope of H5 hemagglutinin to which murine monoclonal antibody H specifically binds. In one embodiment, a monoclonal antibody (either a murine monoclonal antibody or a chimeric or humanized monoclonal antibody) or fragment thereof specifically binds to a conformational epitope of 1-15 hemagglutinin (HA), wherein the conformational epitope is comprised of amino acids 141Pro and 152Lys of the mature HA protein.

In another embodiment, the present invention provides a nucleic acid encoding a monoclonal antibody or antigen binding fragment thereof described herein. In one embodiment the nucleic acid encodes the murine monoclonal antibody C or antigen binding fragment thereof. In another embodiment the nucleic acid encodes the murine monoclonal antibody F or antigen binding fragment thereof. In a further embodiment the nucleic acid encodes the murine monoclonal antibody H or antigen binding fragment thereof. In one embodiment, the present invention provides a vector comprising the nucleic acid. In another embodiment, the present invention proves a cell comprising and expressing the vector.

In one embodiment, humanized antibodies are prepared by combining human heavy and light chain constant regions with the mouse heavy and light chain variable regions using techniques described herein, as well as techniques well known to the skilled artisan. In another embodiment, humanized antibodies are prepared in which DNA sequences are synthesized which encode for humanized $V_L$ and $V_H$ sequences which contain the CDRs of the mouse light and heavy light chain variable regions of a murine monoclonal antibody described herein. In one embodiment, the monoclonal antibody is monoclonal antibody C. In another embodiment, the monoclonal antibody is monoclonal antibody F. In a further embodiment, the monoclonal antibody is monoclonal antibody H.

Methods for synthesizing DNA encoding for a protein of known sequence are well known in the art. Using such methods, DNA sequences which encode the subject humanized antibodies of the present invention are synthesized, and then expressed in vector systems suitable for expression of recombinant antibodies. This may be effected in any vector system which provides for the subject humanized antibody sequences of the present invention, such as expression of fusion proteins comprising the human constant domain sequences and the mouse variable domain sequences which are associated to produce functional (antigen binding) antibodies.

Expression vectors, host cells suitable for expression of recombinant antibodies and humanized antibodies in particular and methods suitable for expression of such antibodies are well known in the art. See, e.g., U.S. Pat. No. 7,074,406.

Host cells known to be capable of expressing functional immunoglobulins include by way of example mammalian cells such as Chinese Hamster Ovary (CHO) cells, COS cells, myeloma cells, bacteria such as *Escherichia coli*, yeast cells such as *Saccharomyces cerevisiae*, among other host cells. Of these, CHO cells are used by many researchers given their ability to effectively express and secrete immunoglobulins.

Essentially, recombinant expression of humanized antibodies is effected by one of two general methods. In the first method, the host cells are transfected with a single vector which provides for the expression of both heavy and light variable sequences fused to selected constant regions. In the second method, host cells are transfected with two vectors, which respectively provide for expression of either the variable heavy or light sequence fused to selected constant regions.

In a second aspect, the present invention provides methods and compositions for the prophylaxis and treatment of H5N1 influenza using a murine monoclonal antibody or fragments thereof described herein. In one embodiment, the present invention provides a pharmaceutical composition comprising a monoclonal antibody described herein and a pharmaceutically acceptable diluent or carrier. In some embodiments, the monoclonal antibody is murine monoclonal antibody C. In other embodiments, the monoclonal antibody is murine monoclonal antibody F. In further embodiments, the monoclonal antibody is murine monoclonal antibody H. In another embodiment, the pharmaceutical composition comprises an antigen binding fragment of a monoclonal antibody described herein and a pharmaceutically acceptable diluent or carrier. In some embodiments, the antigen binding fragment is an antigen binding fragment of murine monoclonal antibody C. In other embodiments, the antigen binding fragment is an antigen binding fragment of murine monoclonal antibody F. In further embodiments, the antigen binding fragment is an antigen binding fragment of monoclonal antibody H. In an additional embodiment, the pharmaceutical composition comprises a nucleic acid molecule encoding said antibody or antibody fragment and a pharmaceutically acceptable diluent or carrier. In a further embodiment, the pharmaceutical composition comprises a vector comprising said nucleic acid and a pharmaceutically acceptable diluent or carrier. In another embodiment, the pharmaceutical composition comprises a cell expressing said vector and a pharmaceutically acceptable diluent or carrier. In an additional embodiment, the pharmaceutical composition comprises a nucleic acid molecule encoding said antibody or antibody fragment and a pharmaceutically acceptable diluent or carrier. In a further embodiment, the pharmaceutical composition comprises a vector comprising said nucleic acid and a pharmaceutically acceptable diluent or carrier. In another embodiment, the pharmaceutical composition comprises a cell expressing said vector and a pharmaceutically acceptable diluent or carrier.

In one embodiment, the present invention provides a method of reducing influenza H5N1 virus infection in a subject, or lowering the risk of influenza H5N1 virus infection in a subject, inhibiting infection of a subject by one or more influenza H5N1 virus strains or isolates of clade 2.3, or prophylaxis of influenza infection or disease by one or more influenza H5N1 virus strains or isolates of clade 2.3. In this embodiment, the method comprises administering to a subject in need thereof, a therapeutically effective amount of a monoclonal antibody or an antigen binding fragment thereof described herein, a nucleic acid molecule comprising a polynucleotide encoding said antibody or antibody fragment; a vector comprising said polynucleotide; or a cell expressing said vector. In one embodiment, the monoclonal antibody is murine monoclonal antibody C. In another embodiment, the monoclonal antibody is murine monoclonal antibody F. In a further embodiment, the monoclonal antibody is murine monoclonal antibody H. In one embodiment, the subject is immunocompromised, is an infant, is a young child or is elderly. In another embodiment, administration provides a therapeutic benefit. In an additional embodiment, therapeutic benefit comprises inhibiting increases in influenza virus titer, decreasing influenza virus titer, inhibiting increases in influenza virus replication, decreasing influenza virus replication, inhibiting increases in influenza virus proliferation or decreasing influenza virus proliferation, or decreasing progression, severity, frequency, duration or probability one or more symptoms or complications associated with influenza virus infection in a subject. In one embodiment, a symptom or complication is selected from chills, fever, cough, sore throat, nasal congestion, sinus congestion, nasal infection, sinus infection, body ache, head ache, fatigue, pneumonia, bronchitis, ear infection, ear ache and death. In another embodiment, the therapeutic benefit comprises hastening a subject's recovery from influenza H5N1 virus infection. In a further embodiment, the agent that is administered to the subject is administered prior to, substantially contemporaneously with or following influenza H5N1 virus infection of the subject.

The antibodies according to the invention can be prepared in a physiologically acceptable formulation and may comprise a pharmaceutically acceptable carrier, diluent and/or excipient using known techniques. For example, the antibody according to the invention and as described herein including any functionally equivalent antibody or functional parts thereof is combined with a pharmaceutically acceptable carrier, diluent and/or excipient to form a therapeutic composition. Suitable pharmaceutical carriers, diluents and/or excipients are well known in the art and include, for example, phosphate buffered saline solutions, water, emulsions such as oil/water emulsions, various types of wetting agents, sterile solutions, etc.

Formulation of the pharmaceutical composition according to the invention can be accomplished according to standard methodology know to those skilled in the art. See, e.g., *Remington: The Science and Practice of Pharmacy,* 21st Ed., Ed. D. B. Troy, Lippincott, Williams & Wilkins, Baltimore, 2006, hereby incorporated by reference herein.

The compositions of the present invention may be administered to a subject in the form of a solid, liquid or aerosol at a suitable, pharmaceutically effective dose. Examples of solid compositions include pills, creams, and implantable dosage units. Pills may be administered orally. Therapeutic creams may be administered topically. Implantable dosage units may be administered locally, for example, at a tumor site, or may be implanted for systematic release of the therapeutic composition, for example, subcutaneously. Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

The compositions may be administered by standard routes of administration. In general, the composition may be administered by topical, oral, rectal, nasal, interdermal, intraperitoneal, or parenteral (for example, intravenous, subcutaneous, or intramuscular) routes. In addition, the composition may be incorporated into sustained release matrices such as biodegradable polymers, the polymers being implanted in the vicinity of where delivery is desired, for example, at the site of a tumor. The method includes administration of a single dose, administration of repeated doses at predetermined time intervals, and sustained administration for a predetermined period of time. A sustained release matrix, as used herein, is a matrix made of materials, usually polymers which are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The composition may be administered in combination with other compositions comprising an biologically active substance or compound, particularly at least one compound selected from the group consisting of compounds against oxidative stress, anti-apoptotic compounds, metal chelators, inhibitors of DNA repair such as pirenzepin and metabolites, 3-amino-1-propanesulfonic acid (3APS), 1,3-propanedisulfonate (1,3PDS), α-secretase activators, β- and γ-secretase inhibitors, tau proteins, neurotransmitter, β-sheet breakers, attractants for amyloid beta clearing/depleting cellular components, inhibitors of N-terminal truncated amyloid beta including pyroglutamated amyloid beta 3-42, anti-inflammatory molecules, "atypical antipsychotics" such as, for example clozapine, ziprasidone, risperidone, aripiprazole or olanzapine or cholinesterase inhibitors (ChEIs) such as tacrine, rivastigmine, donepezil, and/or galantamine, M1 agonists and other drugs including any amyloid or tau modifying drug and nutritive supplements such as, for example, vitamin B12, cysteine, a precursor of acetylcholine, lecithin, choline, Ginkgo biloba, acetyl-L-carnitine, idebenone, propentofylline, or a xanthine derivative, together with an antibody according to the present invention and, optionally, a pharmaceutically acceptable carrier and/or a diluent and/or an excipient and procedures for the treatment of diseases.

Proteinaceous pharmaceutically active matter may be present in amounts between 1 ng and 10 mg per dose. Generally, the regime of administration should be in the range of between 0.1 μg and 10 mg of the antibody according to the invention, particularly in a range 1.0 μg to 1.0 mg, and more particularly in a range of between 1.0 μg and 100 μg, with all individual numbers falling within these ranges also being part of the invention. If the administration occurs through continuous infusion a more proper dosage may be in the range of between 0.01 μg and 10 mg units per kilogram of body weight per hour with all individual numbers falling within these ranges also being part of the invention.

Administration will generally be parenterally, e.g., intravenously. Preparations for parenteral administration include sterile aqueous or non-aqueous solutions, suspensions and emulsions. Non-aqueous solvents include without being limited to it, propylene glycol, polyethylene glycol, vegetable oil such as olive oil, and injectable organic esters such as ethyl oleate. Aqueous solvents may be chosen from the group consisting of water, alcohol/aqueous solutions, emulsions or suspensions including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and others. Preservatives may also be present such as, for example, antimicrobials, anti-oxidants, chelating agents, inert gases, etc.

The pharmaceutical composition may further comprise proteinaceous carriers such as, for example, serum albumin or immunoglobulin, particularly of human origin. Further biologically active agents may be present in the pharmaceutical composition of the invention dependent on the intended use.

In one embodiment, the methods and compositions for the prophylaxis and treatment of H5N1 influenza uses a murine monoclonal antibody or fragments thereof described herein in combination with at least one complementary monoclonal antibody or antibody fragment thereof. According to this embodiment, the use of the complementary Mabs increases protection against circulating strains of H5N1 influenza and to prevent escape mutants. In some embodiments, the methods and compositions use a first murine monoclonal antibody or active fragments thereof described herein in combination with a second complementary murine monoclonal antibody or active fragments thereof. In one embodiment, the first murine monoclonal antibody is monoclonal antibody C. In another embodiment, the first murine monoclonal antibody is monoclonal antibody F. In a further embodiment, the first murine monoclonal antibody is monoclonal antibody H. In one embodiment the second complementary murine monoclonal antibody is monoclonal antibody 2D9. Monoclonal antibody 2D9 is described in Prabakaran et al. (2009) or in PCT International published application number WO 2009/035420. In one embodiment, the monoclonal antibody 2D9 is produced by murine hybridoma 2D9. Murine hybridoma 2D9 was deposited on 10 Jul. 2007 under terms of the Budapest Treaty with the American Type Culture Collection, 10801 University Blvd., Manassas, Va. 20110, USA, and assigned Accession Number PTA-9396. The compositions and methods are as described herein with respect to the use of a single monoclonal antibody or fragment thereof except that the complementary monoclonal antibodies or fragments thereof are used in the methods and compositions.

In a third aspect, the present invention provides methods and compositions for the characterization and/or quantification of H5 expression using a monoclonal antibody or fragments thereof described herein. In some embodiments, the monoclonal antibody is murine monoclonal antibody C. In other embodiments, the monoclonal antibody is murine monoclonal antibody F. In further embodiments, the monoclonal antibody is murine monoclonal antibody H. In one embodiment, the H5 expression relates to the expression of HA of influenza H5N1 viruses. In one embodiment, the composition comprises a monoclonal antibody or fragments thereof described herein. In some embodiments, the monoclonal antibody is murine monoclonal antibody C. In other embodiments, the monoclonal antibody is murine monoclonal antibody F. In further embodiments, the monoclonal antibody is murine monoclonal antibody H. In another embodiment, the method comprises detecting the binding of the H5 with a monoclonal antibody or fragments thereof described herein. In some embodiments, the monoclonal antibody is murine monoclonal antibody C. In other embodiments, the monoclonal antibody is murine monoclonal antibody F. In further embodiments, the monoclonal antibody is murine monoclonal antibody H. In one embodiment, the invention relates to immunofluorescence assays (IFA), immunohistochemical assays and other methods that utilize such binding proteins, including ELISA, hemagglutination inhibition (HI) assays and virus neutralization (VN) assays.

In a fourth aspect, the present invention provides kits and methods for the detection of an influenza A virus in a biological specimen. In one embodiment, the detection relates to the detection of influenza H5N1 viruses. In another embodiment, the detection relates to the detection of influenza H5N1 viruses of the clade 2 family. In a further embodiment, the detection relates to the detection of influenza H5N1 viruses of clade 2.3. In one embodiment, the method comprises contacting the specimen with a first antibody which is a monoclonal antibody or antibody fragment thereof described herein. In some embodiments, the monoclonal antibody is murine monoclonal antibody C. In other embodiments, the monoclonal antibody is murine monoclonal antibody F. In further embodiments, the monoclonal antibody is murine monoclonal antibody H. In another embodiment, the method further comprises contacting the specimen with a second antibody that specifically binds to an epitope of H5 hemagglutinin of an influenza A virus in which the second antibody contains or is conjugated to a detectable element. In some embodiments, the second antibody contains a radioactive atom, is conjugated to a fluorescent molecule, or is conjugated to an enzyme. In other embodiments, the first antibody is immobilized on a solid surface.

In one embodiment, the kit comprises a first antibody which is a monoclonal antibody or antibody fragment thereof described herein together with instructions for performing an assay to detect the influenza A virus. In one embodiment, the kit relates to the detection of influenza H5N1 viruses. In another embodiment, the kit relates to the detection of influenza H5N1 viruses of the clade 2 family. In a further embodiment, the kit relates to the detection of influenza H5N1 viruses of clade 2.3. In some embodiments, the monoclonal antibody is murine monoclonal antibody C. In other embodiments, the monoclonal antibody is murine monoclonal antibody F. In further embodiments, the monoclonal antibody is murine monoclonal antibody H. In another embodiment, the kit further comprises a second antibody that specifically binds to an epitope of H5 hemagglutinin of an influenza A virus in which the second antibody contains or is conjugated to a detectable element. In some embodiments, the second antibody contains a radioactive atom, is conjugated to a fluorescent molecule, or is conjugated to an enzyme. In other embodiments, the first antibody is immobilized on a solid surface. In some embodiments, the kits relate to immunofluorescence assays (IFA), immunohistochemical assays and other methods that utilize such binding proteins, including ELISA, hemagglutination inhibition (HI) assays and virus neutralization (VN) assays. All of these assays are well known to the skilled artisan.

In some embodiments, the methods and kits use a first murine monoclonal antibody or active fragments thereof described herein in combination with a second complementary murine monoclonal antibody or active fragments thereof. In one embodiment, the first murine monoclonal antibody is monoclonal antibody C. In another embodiment, the first murine monoclonal antibody is monoclonal antibody F. In a further embodiment, the first murine monoclonal antibody is monoclonal antibody H. In one embodiment the second complementary murine monoclonal antibody is monoclonal antibody 2D9. The kits and methods are as described herein with respect to the use of a single monoclonal antibody or fragment thereof except that the complementary monoclonal antibodies or fragments thereof are used in the methods and compositions.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference* (RNAi): *The Nuts & Bolts of siRNA Technology*, DNA Press, 2003; Gott, *RNA Interference, Editing, and Modification: Methods and Protocols* (*Methods in Molecular Biology*), Human Press, Totowa, N.J., 2004; Sohail, *Gene Silencing by RNA Interference: Technology and Application*, CRC, 2004.

EXAMPLES

The present invention is described by reference to the following Examples, which is offered by way of illustration and is not intended to limit the invention in any manner. Standard techniques well known in the art or the techniques specifically described below were utilized.

Example 1

Materials and Methods

Viruses and Cells:

The H5N1 viruses used in this studies are from different clades as shown in Table 1 below. Except the Indonesia strains, the remaining H5 influenza viruses were generated with reverse genetics in our lab as described previously (Ho et al., 2009). Viruses were inoculated into the allantoic cavities of 11-day-old embryonated chicken eggs and harvested following 48 h of incubation at 37° C. Virus titers were determined using hemagglutination assays according to standard methods (Abdel-Ghafar et al., 2008). H5N1 subtype viruses were inactivated with formaldehyde as described previously (He et al., 2007). All experiments with live H5N1 subtype viruses were performed in a biosafety level 3 containment laboratory in compliance with CDC/NIH and WHO recommendations and also were approved by the Agri-Food and Veterinary Authority and the Ministry of Health of Singapore.

MDCK cells were obtained from the American Type Culture Collection (ATCC). Cells were propagated in Dulbecco's minimal essential medium (DMEM) supplemented with 10% fetal bovine serum. Virus stocks were grown in MDCK cells in DMEM supplemented with 0.5% bovine serum albumin (BSA) and 200 ng/ml of trypsin.

MAb Production:

BALB/c mice were immunized twice subcutaneously at regular intervals of 2 weeks with inactivated whole virus from A/Anhui/1/05 at HA titer of $2^8$ in 0.1 ml of Phosphate Buffered Saline (PBS), which was emulsified with an equal volume of Montanide ISA 563 adjuvant (SEPPIC, France). Mice were boosted with the same viral antigen, 3 days before the fusion of splenocytes with SP2/0 cells. The fused cells were seeded in 96-well plates, and their supernatants were screened by immunofluorescence assays as described below. The hybridomas that produced the Mabs were cloned by limiting dilution at least three times. The positive Mabs were tested for their hemagglutination inhibition activity as described below. Immunoglobulins from selected positive mAbs were isotyped using a commercial isotyping kit (Amersham Bioscience, England) as described in the manufacturer's protocol.

Immunofluorescence Assay (IFA):

MDCK cells cultured in 96-well plates were infected with AIV H5N1 strains. At 24-48 h post-infection, the cells were fixed with 4% paraformaldehyde for 30 min at room temperature and washed thrice with phosphate buffered saline (PBS), pH 7.4. Fixed cells were incubated with hybridoma culture supernatant at 37° C. for 1 h, rinsed with phosphate buffered saline (PBS) and then incubated with a 1:400 dilution of fluorescein isothiocyanate (FITC)-conjugated rabbit anti-mouse Immunoglobulin (Dako, Denmark). Cells were rinsed again in PBS and antibody binding was evaluated by widefield epi-fluorescence microscopy (Olympus IX71).

Hemagglutination Inhibition Assay:

Hemagglutination inhibition (HI) assays were performed as described previously (Webster et al., 1991). Briefly, Mabs were serially diluted (2 fold) in V-bottom 96-well plates and mixed with 4 HA units of H5N1 viruses. Plates were incubated for 30 min at room temperature, and 1% chicken RBCs were added to each well. The hemagglutination inhibition endpoint was the highest Mab dilution in which agglutination was not observed.

Microneutralization Assay:

Neutralization activity of the monoclonal antibody against H5N1 strains was analyzed by microneutralization assay as previously described (Prabakaran et al., 2008). Briefly, ten times diluted Mab was further serially diluted (two-fold) and incubated with 100 50% tissue culture infectious doses (TCID50) of different clades of H5N1 strains for 1 h at room temperature and plated in duplicate onto MDCK cells grown in a 96-well plate. The TCID50 of each of the H5N1 strains in MDCK cell culture was determined by the Reed and Muench method. The neutralizing titer was assessed as the highest Mab dilution in which no cytopathic effect was observed by light microscopy.

Isolation and Analysis of Escape Mutants:

The epitopes recognized by the Mabs were mapped by characterization of escape mutants as described previously (Kaverin et al., 2007). Briefly, H5N1 viruses were incubated with an excess of Mab for 1 h and then inoculated into 11 day old embryonated chicken eggs. The eggs were incubated at 37° C. for 24-48 h. Virus was harvested and used for cloning in limiting dilution in embryonated chicken eggs and the escape mutants were plaque purified. RNA was extracted from the allantoic fluid. The hemagglutinin gene was reverse transcriptase (RT)-PCR amplified and cloned into a TA-cloning vector (Promega) and several clones were sequenced. The sequences of individual clones were analyzed by comparison with the sequences of the parent virus.

Example 2

Characterization of Murine Monoclonal Antibody C, F and H

Mab C, F and H were produced from mice immunized with A/Anhui/1/05 H5N1 virus. Mab C and H were identified to belong to isotype IgG2a, while Mab F belongs to IgG3. All three of these Mabs present neutralizing activity against H5N1 strain A/Anhui/1/05 H5N1 (Anhui), besides positive activity in IFA with Anhui infected MDCK cells (FIG. 1), indicating that they all recognize neutralizing epitopes in H5.

Example 3

Complementary Neutralization with Mab 2D9 by Either Mab C, F or H

H1 and microneutralization tests were performed with Mab C, F and H against a range of H5N1 viruses from different major clades. As shown in Tables 1 and 2, Mab C, F and H can efficiently neutralize H5N1 viruses of clade 2.3. Besides, these three Mabs are able to react with some of H5N1 viruses of clade 2.2. Mab C can neutralize more viruses from clade 2.2 used in this study than Mab F and H. None of them can react with viruses from clade 0 and 1.0. As shown previously, Mab 2D9 can neutralize different H5N1 viruses from different clades but can not inhibit viruses of clade 2.3 efficiently. The Mab mix with Mab 2D9 and Mab C was shown to be able to neutralize all the viruses from all major clades used in this study. The neutralization efficacy of 2D9+C was found to be better than Mab 2D9 with Mab 4C2.

TABLE 1

Hemagglutination Inhibition Titer of Mabs[a,b]

| Viruses | Clade | 2D9 | C | F | H |
|---|---|---|---|---|---|
| A/Hongkong/156/97 | 0 | 256 | <8 | <8 | <8 |
| A/HongKong/213/03 | 1 | 256 | <8 | <8 | <8 |
| A/Vietnam/1203/04 | 1 | 256 | <8 | <8 | <8 |
| A/MuscovyduckVietnam/33/07 | 1 | 128 | <8 | <8 | <8 |
| A/Indonesia/CDC594/06 | 2.1.2 | 256 | 16 | 16 | 16 |
| A/Indonesia/CDC669/06 | 2.1.3 | 256 | 256 | 128 | 64 |
| A/Indonesia/CDC623/06 | 2.1.3 | 128 | 256 | 256 | 64 |
| A/muscovy duck/Rostovon Don/51/07 | 2.2 | 128 | <8 | <8 | <8 |
| A/barheaded goose/Qinghai/12/05 | 2.2 | 256 | 256 | 256 | <8 |
| A/chicken/Guangdong/178/04 | 2.2 | 256 | <8 | <8 | <8 |
| A/Turkey/Turkey1/05 | 2.2 | 256 | 128 | 64 | <8 |
| A/Nigeria/6e/07 | 2.2 | 256 | 256 | 128 | <8 |
| A/Anhui/1/05 | 2.3 | 128 | 256 | 256 | 256 |
| A/VietNam/HN31242/07 | 2.3 | 64 | 128 | 64 | 64 |
| A/Jiangsu/2/07 | 2.3 | <8 | 256 | 64 | 64 |
| A/goose/Guiyang/337/06 | 4 | 128 | 32 | 32 | <8 |
| A/chicken/Shanxi/2/06 | 7 | 256 | 128 | 64 | <8 |
| A/chicken/Henan/12/04 | 8 | 256 | <8 | <8 | <8 |

[a]Concentration of MAb at 0.15 mg/ml.
[b]4 HA unit of each virus strain used for HI.

TABLE 2

Neutralization Titer With Different Mab or Mab Mix[a,b]

| Viruses | Clade | 2D9 | C | F | H | 2D9 + C | 2D9 + 4C2 |
|---|---|---|---|---|---|---|---|
| A/Hongkong/156/97 | 0 | 64 | <8 | <8 | <8 | 32 | 32 |
| A/Vietnam/1203/04 | 1 | 64 | <8 | <8 | <8 | 32 | 32 |

TABLE 2-continued

Neutralization Titer With Different Mab or Mab Mix[a,b]

| Viruses | Clade | 2D9 | C | F | H | 2D9 + C | 2D9 + 4C2 |
|---|---|---|---|---|---|---|---|
| A/Indonesia/CDC594/06 | 2.1.2 | 128 | <8 | <8 | <8 | 64 | 128 |
| A/Indonesia/CDC669/06 | 2.1.3 | 128 | 128 | 128 | 64 | 128 | 128 |
| A/muscovy duck/Rostovon Don/51/07 | 2.2 | 128 | <8 | <8 | <8 | 64 | 64 |
| A/barheaded goose/Qinghai/12/05 | 2.2 | 128 | 64 | 32 | <8 | 128 | 128 |
| A/Anhui/1/05 | 2.3 | 64 | 128 | 128 | 128 | 128 | 32 |
| A/VietNam/HN31242/07 | 2.3 | 16 | 128 | 64 | 64 | 64 | 16 |
| A/Jiangsu/2/07 | 2.3 | <8 | 128 | 64 | 64 | 64 | <8 |
| A/goose/Guiyang/337/06 | 4 | 64 | <8 | <8 | <8 | 32 | 32 |
| A/chicken/Shanxi/2/06 | 7 | 64 | 16 | <8 | <8 | 32 | 32 |
| A/chicken/Henan/12/04 | 8 | 64 | <8 | <8 | <8 | 32 | 32 |

[a]Concentration of MAb at 0.15 mg/ml.
[b]One hundred TCID50 of each virus strain used for microneutralization assays.

Example 4

Epitope Mapping for Mab C, F and H

Since the three Mabs are able to neutralize A/Anhui/1/05 H5N1 virus, the amino acids involved in forming the epitopes of the three Mabs were analyzed using selection of neutralization escape mutants. The nucleotide sequence encoding the HA protein including signal protein is set forth in SEQ ID NO:1, and the amino acid sequence of the HA protein including signal protein is set forth in SEQ ID NO:2. The nucleotide sequence encoding the mature HA protein is set forth in SEQ ID NO:3, and the amino acid sequence of the mature HA protein is set forth in SEQ ID NO:4. Sequencing of the complete HA gene isolated from multiple escape variants to Mab C carried single point mutations at amino acid positions 152 (Lys to Glu), 184 (Ala to Gly) and 194 (Pro to Leu) (excluding signal peptide) (Table 3). Escape mutants from Mab F were identified to contain mutations with both amino acid 152 (Lys to Glu) and 221 (Gly to Arg) on H5 protein (excluding signal peptide). Escape mutants from Mab H present amino acid substitutions on both 141 (Pro to Leu) and 152 (Lys to Glu) of H5 protein (excluding signal peptide).

TABLE 3

Neutralizing Epitopes of H5 HA using Mab C, F and H by Escape Mutations

| Parental Virus | Mab | Nucleotide | Nucleotide Change | Amino acid | Amino acid Change |
|---|---|---|---|---|---|
| A/Anhui/1/05 | C | 454 | A to G | 152 | Lys to Glu |
|  |  | 551 | C to G | 184 | Ala to Gly |
|  |  | 581 | C to T | 194 | Pro to Leu |
|  | F | 454 | A to G | 152 | Lys to Glu |
|  |  | 661 | G to A | 221 | Gly to Arg |
|  | H | 422 | C to T | 141 | Pro to Leu |
|  |  | 454 | A to G | 152 | Lys to Glu |

As shown by the above Examples, Mab C, F and H generated from mice immunized with Anhui H5N1 virus are able to recognize H5 viruses from clade 2.3. The efficient reactivity was observed in IFA, HI and virus neutralization. Mab C presents broader neutralization than Mab F and H as it can efficiently neutralize more viruses from clade 2.2 and 4. Mab C targets amino acid positions 152 (Lys to Glu), 184 (Ala to Gly) and 194 (Pro to Leu) (excluding signal peptide). Escape mutants from Mab F were identified to contain mutations with both amino acid 152 (Lys to Glu) and 221 (Gly to Arg) on 1-15 protein (excluding signal peptide). Escape mutants from Mab H present amino acid substitutions on both 141 (Pro to Leu) and 152 (Lys to Glu) of H5 protein (excluding signal peptide). Mab C, together with Mab 2D9, can neutralize all the viruses of different clades, as a universal therapeutic Mab pair.

Example 5

Production of Antibodies and Antibody Fragments

The monoclonal antibodies of the present invention can be produced by any technique that provides for the production of antibody molecules by continuous cell lines in culture. Such methods include, but are not limited to, the hybridoma technique originally developed in 1975 by Kohler and Milstein (*Nature* 256:495-497), as well as the trioma technique, the human B-cell hybridoma technique (Kozbor et al., 1983, *Immunology Today* 4:72) and the EBV-hybridoma technique to produce human monoclonal antibodies (Cole et al., in *Monoclonal Antibodies and Cancer Therapy* Alan R. Liss, Inc., pp 77-96 (1985)). Human antibodies can be used and can be obtained by using human hybridomas (Cote et al., 1983, *Proc. Nat=l. Acad. Sci. U.S.A.*, 80:2026-2030) or by transforming human B cells with EBV virus in vitro (Cole et al., 1985, in Monoclonal Antibodies and Cancer Therapy, Alan R. Liss, pp. 77-96). Moreover, techniques developed for the production of "chimeric antibodies" or "humanized antibodies" (Morrison et al., 1984, *J. Bacteriol.* 159-870; Neuberger et al., 1984, *Nature* 312:604-608; Takeda et al., 1985, *Nature* 314:452-454) by introducing sequences from a murine antibody molecule of the present invention, e.g., mAb C, F or H, together with genes from a human antibody molecule of appropriate biological activity can be used. Chimeric antibodies are those that contain a human Fc portion and a murine (or other non-human) Fv portion. Humanized antibodies are those in which the murine (or other non-human) complementarity determining regions (CDR) are incorporated into a human antibody. Both chimeric and humanized antibodies are monoclonal. Such human or humanized chimeric antibodies are preferred for use in in vivo diagnosis or therapy of human diseases or disorders.

According to the invention, techniques described for the production of single chain antibodies (U.S. Pat. No. 4,946,778) can be adapted to provide single chain antibodies of the present invention. An additional embodiment of the invention utilizes the techniques described for the construction of Fab expression libraries (Huse et al., 1989, *Science* 246: 1275-1281) to allow rapid and easy identification of monoclonal Fab fragments with the desired specificity for an antibody of the present invention, or its derivatives, or analogs.

Antibody fragments that contain the idiotype of the antibody molecule can be generated by known techniques. For example, such fragments include but are not limited to: the F(ab=)$_2$ fragment which can be produced by pepsin digestion of the antibody molecule; the Fab= fragments which can be generated by reducing the disulfide bridges of the F(ab=)$_2$ fragment, and the Fab fragments which can be generated by treating the antibody molecule with papain and a reducing agent. Such antibody fragments can be generated from any of the polyclonal or monoclonal antibodies of the invention.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), immunofluorescence assays and immunoelectrophoresis assays, etc. In one embodiment, antibody binding is detected by detecting a label on the primary antibody. In another embodiment, the primary antibody is detected by detecting binding of a secondary antibody or other reagent to the primary antibody. In a further embodiment, the secondary antibody is labeled. Means are known in the art for detecting binding in an immunoassay.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Abdel-Ghafar A N, Chotpitayasunondh T, Gao Z, Hayden F G, Nguyen D H, de Jong M D, Naghdaliyev A, Peiris J S, Shindo N, Soeroso S et al. (2008). Update on avian influenza A (H5N1) virus infection in humans. *N Engl J Med* 358:261-273.

Beigel J H, Farrar J, Han A M, Hayden F G, Hyer R, de Jong M D, Lochindarat S, Nguyen T K, Nguyen T H, Tran T H et al. (2005). Avian influenza A (H5N1) infection in humans. *N Engl J Med* 353:1374-1385.

Chothia C and Lesk A M (1987). Canonical structures for the hypervariable regions of immunoglobulins. *J Mol Biol* 196:901-917.

de Jong M D and Hien T T (2006). Avian influenza A (H5N1). *J Clin Virol* 35:2-13.

de Jong M D, Tran T T, Truong H K, Vo M H, Smith G J, Nguyen V C, Bach V C, Phan T Q, Do Q H, Guan Y et al. (2005). Oseltamivir resistance during treatment of influenza A (H5N1) infection. *N Engl J Med* 353:2667-2672.

He Q, Velumani S, Du Q, Lim C W, Ng F K, Donis R, Kwang J (2007). Detection of H5 avian influenza viruses by antigen-capture enzyme-linked immunosorbent assay using H5-specific monoclonal antibody. *Clin Vaccine Immunol* 14:617-623.

Hieter P A, Max E E, Seidman J G, Maizel J V Jr, Leder P (1980). Cloned human and mouse kappa immunoglobulin constant and J region genes conserve homology in functional segments. *Cell* 22:197-207.

Ho H T, Qian H L, He F, Meng T, Szyporta M, Prabhu N, Prabakaran M, Chan K P, Kwang J (2009). Rapid detection of H5N1 subtype influenza viruses by antigen capture enzyme-linked immunosorbent assay using H5- and N1-specific monoclonal antibodies. *Clin Vaccine Immunol* 16:726-732.

Huston J S, Levinson D, Mudgett-Hunter M, Tai M S, Novotný J, Margolies M N, Ridge R J, Bruccoleri R E, Haber E, Crea R, et al. (1988). Protein engineering of antibody binding sites: recovery of specific activity in an anti-digoxin single-chain Fv analogue produced in *Escherichia coli*. *Proc Nat Acad Sci USA* 85:5879-5883.

Johnson G and Wu T T (2000). Matching amino acid and nucleotide sequences of mouse rheumatoid factor CDRH3-FRH4 segments to other mouse antibodies with known specificities. *Bioinformatics* 16:941-943.

Kabat E A, Wu T T, Perry H M, Gottesman K S, Foeller C (1992). *Sequences of Proteins of Immunological Interest*, U.S. Department of Health and Human Services.

Kaverin N V, Rudneva I A, Govorkova E A, Timofeeva T A, Shilov A A, Kochergin-Nikitsky K S, Krylov P S, Webster R G (2007). Epitope mapping of the hemagglutinin molecule of a highly pathogenic H5N1 influenza virus by using monoclonal antibodies. *J Virol* 81:12911-12917.

Khaw B A, Strauss H W, Carvalho A, Locke E, Gold H K, Haber E (1982). Technetium-99m labeling of antibodies to cardiac myosin Fab and to human fibrinogen. *J Nucl Med* 23:1011-1019.

Le M T, Wertheim H F, Nguyen H D, Taylor W, Hoang P V, Vuong C D, Nguyen H L, Nguyen H H, Nguyen T Q, Nguyen T V et al. (2008). Influenza A H5N1 clade 2.3.4 virus with a different antiviral susceptibility profile replaced clade 1 virus in humans in northern Vietnam. *PLoS One* 3(10):e3339.

Prabakaran M, Velumani S, He F, Karuppannan A K, Geng G Y, et al. (2008) Protective immunity against influenza H5N1 virus challenge in mice by intranasal co-administration of baculovirus surface-displayed HA and recombinant CTB as an adjuvant. *Virology* 380:412-420.

Prabakaran M, Prabhu N, He F, Hongliang Q, Ho H T, Qiang J, Meng T, Goutama M, Kwang J (2009). Combination therapy using chimeric monoclonal antibodies protects mice from lethal H5N1 infection and prevents formation of escape mutants. *PLoS One* 4(5):e5672.

Rader C, Cheresh D A, Barbas C F 3rd (1998). A phage display approach for rapid antibody humanization: designed combinatorial V gene libraries. *Proc Natl Acad Sci USA* 95:8910-8915.

Riechmann L, Clark M, Waldmann H, Winter G (1988). Reshaping human antibodies for therapy. *Nature* 332:323-327.

Rousseaux J, Rousseaux-Prevost R, Bazin H (1986). Optimal conditions for the preparation of proteolytic fragments from monoclonal IgG of different rat IgG subclasses. *Methods Enzymology* 121:663-69, Academic Press.

Webster R G, Kawaoka Y, Taylor J, Weinberg R, Paoletti E (1991). Efficacy of nucleoprotein and hemagglutinin antigens expressed in fowlpox virus as vaccine for influenza in chickens. *Vaccine* 9:303-308.

What is claimed is:

1. An antibody or antigen binding fragment that specifically binds to a conformational epitope of influenza virus H5 hemagglutinin (HA) that murine monoclonal antibody C produced by murine hybridoma C which is deposited with Cell-Bank Australia with Accession Number CBA20110011 specifically binds, wherein the conformational epitope is comprised of amino acid 152Lys, 184Ala and 194Pro of the mature HA protein having the sequence set forth in SEQ ID NO:4 and wherein the antibody or antigen binding fragment is a murine monoclonal antibody C, a single chain antibody thereof, a chimeric antibody thereof, a single chain antibody of the chimeric antibody, a humanized antibody thereof, a single chain antibody of the humanized antibody or antibody fragments thereof.

2. A murine monoclonal antibody C as produced by murine hybridoma C which is deposited with the CellBank Australia with Accession Number CBA20110011.

3. A method for detecting an influenza A virus in a biological specimen which comprises contacting the specimen with a first antibody, wherein the first antibody is the antibody or antigen binding fragment of claim 1.

4. The method of claim 3, which further comprises contacting the specimen with a second antibody that specifically binds to an epitope of H5 hemagglutinin of an influenza A virus, wherein said second antibody contains or is conjugated to a detectable element.

5. The method of claim 4, wherein the first antibody is immobilized onto a solid surface.

6. The method of claim 4, wherein the second antibody contains a radioactive atom, is conjugated to a fluorescent molecule, or is conjugated to an enzyme.

7. The method of claim 3, wherein the influenza A virus is an influenza H5N1 virus.

8. The method of claim 7, wherein the influenza H5N1 virus is an influenza H5N1 virus of the Glade 2 family.

9. The method of claim 8, wherein the influenza H5N1 virus is an influenza H5N1 virus of Glade 2.3.

10. The method of claim 3, wherein a complementary monoclonal antibody is used in combination with the first antibody.

11. The method of claim 10, wherein the complementary monoclonal antibody is monoclonal antibody 2D9 as produced by hybridoma 2D9 which is deposited with the American Type Culture Collection with Accession Number PTA-9396.

12. A kit for detecting an H5 influenza A virus in a biological specimen which comprises a first antibody, wherein the first antibody is the antibody or antigen binding fragment of claim 1 together with instructions for performing an assay to detect the influenza A virus.

13. The kit of claim 12, which further comprises a second antibody that specifically binds to an epitope of H5 hemagglutinin of an influenza A virus, wherein said second antibody contains or is conjugated to a detectable element.

14. The kit of claim 12, wherein the H5 influenza A virus is an influenza H5N1 virus.

15. The kit of claim 14, wherein the influenza H5N1 virus is an influenza H5N1 virus of the Glade 2 family.

16. The kit of claim 15, wherein the influenza H5N1 virus is an influenza H5N1 virus of Glade 2.3.

17. The kit of claim 12, wherein a complementary monoclonal antibody is used in combination with the first antibody.

18. The kit of claim 17, wherein the complementary monoclonal antibody is monoclonal antibody 2D9 as produced by hybridoma 2D9 which is deposited with the American Type Culture Collection with Accession Number PTA-9396.

19. A composition comprising an agent and a pharmaceutically acceptable diluent or carrier, wherein the agent is the antibody or antigen binding fragment of claim 1.

20. A composition comprising an agent and a pharmaceutically acceptable diluent or carrier, wherein the agent is a combination of the antibody or antigen binding fragment of claim 1 and at least one complementary monoclonal antibody or fragment thereof.

21. The composition of claim 20, wherein the complementary monoclonal antibody is murine monoclonal antibody 2D9 as produced by hybridoma 2D9 which is deposited with the American Type Culture Collection with Accession Number PTA-9396.

22. A method of reducing influenza H5N1 virus infection in a subject, or lowering the risk of influenza H5N1 virus infection in a subject, or inhibiting infection of a subject by one or more influenza H5N1 virus strains or isolates, or prophylaxis of influenza infection or disease by one or more influenza H5N1 virus strains or isolates which comprises administering to a subject in need thereof, a therapeutically effective amount of an agent, wherein the agent is the antibody or antigen binding fragment of claim 1.

23. The method of claim 22, wherein the subject is immunocompromised, an infant, a young child or elderly.

24. The method of claim 22, wherein the administration provides a therapeutic benefit.

25. The method of claim 24, wherein the therapeutic benefit comprises (a) inhibiting increases in influenza virus titer, (b) decreasing influenza virus titer, (c) inhibiting increases in influenza virus replication, (d) decreasing influenza virus replication, (e) inhibiting increases in influenza virus proliferation or decreasing influenza virus proliferation, (f) decreasing progression, severity, frequency, or duration of one or more symptoms or complications associated with influenza virus infection in a subject or (g) hastening a subject's recovery from influenza virus infection.

26. The method of claim 25, wherein a symptom or complication is selected from chills, fever, cough, sore throat, nasal congestion, sinus congestion, nasal infection, sinus infection, body ache, head ache, fatigue, pneumonia, bronchitis, ear infection, ear ache and death.

27. The method of claim 22, wherein the influenza A virus is an H5N1 subtype of clade 2.3.

28. A method of reducing influenza H5N1 virus infection in a subject, or lowering the risk of influenza H5N1 virus infection in a subject, or inhibiting infection of a subject by one or more influenza H5N1 virus strains or isolates, or prophylaxis of influenza infection or disease by one or more influenza H5N1 virus strains or isolates which comprises administering to a subject in need thereof, a therapeutically effective amount of an agent, wherein the agent is a combination of the antibody or antigen binding fragment of claim 1 and at least one complementary monoclonal antibody or antigen binding fragment.

29. The method of claim 28, wherein the complementary monoclonal antibody is murine monoclonal antibody 2D9 as produced by hybridoma 2D9 which is deposited with the American Type Culture Collection with Accession Number PTA-9396.

30. The method of claim 28, wherein the subject is immunocompromised, an infant, a young child or elderly.

31. The method of claim 28, wherein the administration provides a therapeutic benefit.

32. The method of claim 31, wherein the therapeutic benefit comprises (a) inhibiting increases in influenza virus titer, (b) decreasing influenza virus titer, (c) inhibiting increases in influenza virus replication, (d) decreasing influenza virus replication, (e) inhibiting increases in influenza virus proliferation or decreasing influenza virus proliferation, (f) decreasing progression, severity, frequency, or duration of one or more symptoms or complications associated with influenza virus infection in a subject or (g) hastening a subject's recovery from influenza virus infection.

33. The method of claim 32, wherein a symptom or complication is selected from chills, fever, cough, sore throat, nasal congestion, sinus congestion, nasal infection, sinus infection, body ache, head ache, fatigue, pneumonia, bronchitis, ear infection, ear ache and death.

34. A method for characterizing and/or quantifying H5 expression in a sample, the method comprises contacting the sample with a first antibody, wherein the first antibody is the antibody or antigen binding fragment of claim 1.

35. The method of claim 34, which further comprises contacting the sample with a second antibody that specifically binds to an epitope of H5 hemagglutinin of an influenza A virus, wherein said second antibody contains or is conjugated to a detectable element.

36. The method of claim 35, wherein the first antibody is immobilized onto a solid surface.

37. The method of claim 35, wherein the second antibody contains a radioactive atom, is conjugated to a fluorescent molecule, or is conjugated to an enzyme.

38. A kit for characterizing and/or quantifying H5 expression in a sample, which kit comprises a first antibody, wherein the first antibody is the antibody or antigen binding fragment of claim 1 together with instructions for performing an assay to characterize and/or quantify H5 expression in the sample.

39. The kit of claim 38, which further comprises a second antibody that specifically binds to an epitope of H5 hemagglutinin of an influenza A virus, wherein said second antibody contains or is conjugated to a detectable element.

* * * * *